US008617533B2

(12) United States Patent
Smith et al.

(10) Patent No.: US 8,617,533 B2
(45) Date of Patent: *Dec. 31, 2013

(54) MULTI-ANTIGENIC ALPHAVIRUS REPLICON PARTICLES AND METHODS

(75) Inventors: Jonathan F. Smith, Cary, NC (US); Kurt Kamrud, Apex, NC (US); Sergey Dryga, Chapel Hill, NC (US); Ian Caley, Durham, NC (US)

(73) Assignee: AlphaVax, Inc., Research Triangle Park, NC (US)

( * ) Notice: Subject to any disclaimer, the term of this patent is extended or adjusted under 35 U.S.C. 154(b) by 637 days.

This patent is subject to a terminal disclaimer.

(21) Appl. No.: 12/116,031

(22) Filed: May 6, 2008

(65) Prior Publication Data

US 2008/0213309 A1    Sep. 4, 2008

Related U.S. Application Data

(62) Division of application No. 10/735,601, filed on Dec. 12, 2003, now abandoned.

(60) Provisional application No. 60/433,299, filed on Dec. 13, 2002, provisional application No. 60/433,058, filed on Dec. 13, 2002.

(51) Int. Cl.
*A01N 63/00* (2006.01)
*A61K 48/00* (2006.01)
*C12N 15/00* (2006.01)
*C12N 15/86* (2006.01)
*C12N 15/88* (2006.01)
*C12N 15/87* (2006.01)

(52) U.S. Cl.
USPC .......... 424/93.2; 435/455; 435/458; 435/461; 435/465

(58) Field of Classification Search
None
See application file for complete search history.

(56) References Cited

U.S. PATENT DOCUMENTS

| | | |
|---|---|---|
| 4,650,764 A | 3/1987 | Temin et al. |
| 4,708,871 A | 11/1987 | Geysen |
| 5,091,309 A | 2/1992 | Schlesinger et al. |
| 5,185,440 A | 2/1993 | Davis et al. |
| 5,217,879 A | 6/1993 | Huang et al. |
| 5,505,947 A | 4/1996 | Johnston et al. |
| 5,521,082 A | 5/1996 | Lewis et al. |
| 5,639,650 A | 6/1997 | Johnston et al. |
| 5,703,057 A | 12/1997 | Johnston et al. |
| 5,726,022 A | 3/1998 | Burmer |
| 5,739,026 A | 4/1998 | Garoff et al. |
| 5,766,602 A | 6/1998 | Xiong et al. |
| 5,789,245 A | 8/1998 | Dubensky, Jr. et al. |
| 5,792,462 A | 8/1998 | Johnston et al. |
| 5,811,407 A | 9/1998 | Johnston et al. |
| 5,814,482 A | 9/1998 | Dubensky, Jr. et al. |
| 5,827,658 A | 10/1998 | Liang |
| 5,831,016 A | 11/1998 | Wang et al. |
| 5,843,723 A | 12/1998 | Dubensky, Jr. et al. |
| 5,853,719 A | 12/1998 | Nair et al. |
| 5,866,553 A | 2/1999 | Donnelly et al. |
| 5,958,738 A | 9/1999 | Lindemann et al. |
| 5,989,553 A | 11/1999 | Johnston et al. |
| 6,008,035 A | 12/1999 | Johnston et al. |
| 6,015,686 A | 1/2000 | Dubensky, Jr. et al. |
| 6,015,694 A | 1/2000 | Dubensky, Jr. et al. |
| 6,146,874 A | 11/2000 | Zolotukhin et al. |
| 6,156,558 A | 12/2000 | Johnston et al. |
| 6,190,666 B1 | 2/2001 | Garoff et al. |
| 6,194,191 B1 | 2/2001 | Zhang et al. |
| 6,197,502 B1 | 3/2001 | Renner et al. |
| 6,224,879 B1 | 5/2001 | Sjoberg et al. |
| 6,235,290 B1 | 5/2001 | Brunham |
| 6,242,259 B1 | 6/2001 | Polo et al. |
| 6,261,570 B1 | 7/2001 | Parker et al. |
| 6,267,967 B1 | 7/2001 | Johnston et al. |
| 6,306,388 B1 | 10/2001 | Nair et al. |
| 6,309,642 B1 | 10/2001 | Cutler et al. |
| 6,329,201 B1 | 12/2001 | Polo et al. |
| 6,342,372 B1 | 1/2002 | Dubensky, Jr. et al. |
| 6,376,236 B1 | 4/2002 | Dubensky, Jr. et al. |
| 6,391,632 B1 | 5/2002 | Dubensky, Jr. et al. |
| 6,426,196 B1 | 7/2002 | Dubensky, Jr. et al. |
| 6,451,592 B1 | 9/2002 | Dubensky, Jr. et al. |
| 6,485,958 B2 | 11/2002 | Blanch et al. |
| 6,495,143 B2 | 12/2002 | Lee et al. |
| 6,517,842 B1 | 2/2003 | Hevey et al. |

(Continued)

FOREIGN PATENT DOCUMENTS

| | | |
|---|---|---|
| WO | 92/10578 | 6/1992 |
| WO | 95/07994 | 3/1995 |

(Continued)

OTHER PUBLICATIONS

Klimstra, et al. (1998) Journal of Virology, 72(9): 7357-66.*
Strauss, et al. (1980) "Growth and Release of Several Alphaviruses in Chick and BHK Cells", Journal of General Virology, 49: 297-307.*
Bishop, et al. (Feb. 1976) "Effect of Medium of Lowered NaCl Concentration of Virus Release and Protein Synthesis in Cells Infected with Reticuloendotheliosis Virus", Journal of Virology, 17(2): 446-52.*
Balasuriya et al. (Feb. 2002) "Alphavirus replicon particles expressing the two major envelope proteins of equine arteritis virus induce high level protection against challenge with virulent virus in vaccinated horses"; *Vaccine* 20:1609-1617.

(Continued)

*Primary Examiner* — Robert M Kelly
(74) *Attorney, Agent, or Firm* — Lathrop & Gage LLP

(57) ABSTRACT

Viral replicon selected nucleic acid expression libraries are useful for analyzing multiple antigens associated with a parasite, pathogen or neoplasia or for preparing immunogenic compositions for generating immune responses specific for the parasite, pathogen or neoplasia. Alphavirus replicon particles representative of the nucleic acid expression library are preferred. The nucleic acid library can be a random library, or it can be prepared after a selection step, for example, by differential hybridization prior to cloning into the replicon vector.

19 Claims, 1 Drawing Sheet

(56) References Cited

U.S. PATENT DOCUMENTS

| | | | |
|---|---|---|---|
| 6,521,235 | B2 | 2/2003 | Johnston et al. |
| 6,531,135 | B1 | 3/2003 | Johnston et al. |
| 6,541,010 | B1 | 4/2003 | Johnston et al. |
| 6,583,121 | B1 | 6/2003 | Johnston et al. |
| 6,632,640 | B1 | 10/2003 | Lee et al. |
| 6,767,699 | B2 | 7/2004 | Polo et al. |
| 6,770,283 | B1 | 8/2004 | Garoff et al. |
| 6,770,479 | B1 | 8/2004 | Lee et al. |
| 6,783,939 | B2 | 8/2004 | Olmsted et al. |
| 6,844,188 | B1 | 1/2005 | MacDonald et al. |
| 7,078,218 | B2 | 7/2006 | Smith et al. |
| 7,090,852 | B2 | 8/2006 | Hevey et al. |
| 2002/0018766 | A1 | 2/2002 | Roberts et al. |
| 2002/0034521 | A1 | 3/2002 | Lee et al. |
| 2002/0102273 | A1 | 8/2002 | Grieve et al. |
| 2002/0141975 | A1 | 10/2002 | Olmsted et al. |
| 2002/0164582 | A1 | 11/2002 | Hart et al. |
| 2003/0021766 | A1 | 1/2003 | Vadjy et al. |
| 2003/0091591 | A1 | 5/2003 | Xiong et al. |
| 2003/0119182 | A1 | 6/2003 | Smith et al. |
| 2003/0148262 | A1 | 8/2003 | Polo et al. |
| 2003/0232035 | A1 | 12/2003 | Dubensky et al. |
| 2004/0029278 | A1 | 2/2004 | Dubensky et al. |
| 2004/0166573 | A1 | 8/2004 | Smith et al. |
| 2004/0208848 | A1 | 10/2004 | Smith et al. |
| 2004/0235133 | A1 | 11/2004 | Frolov et al. |
| 2005/0054107 | A1 | 3/2005 | Chulay et al. |
| 2005/0123555 | A1 | 6/2005 | Olmsted et al. |
| 2005/0266550 | A1 | 12/2005 | Rayner et al. |
| 2006/0099587 | A1 | 5/2006 | Johnson et al. |
| 2011/0027306 | A1 | 2/2011 | Rayner et al. |

FOREIGN PATENT DOCUMENTS

| | | |
|---|---|---|
| WO | 95/27044 | 10/1995 |
| WO | 95/31565 | 11/1995 |
| WO | 96/17072 | 6/1996 |
| WO | 96/37220 | 11/1996 |
| WO | 96/37616 | 11/1996 |
| WO | 99/08706 | 2/1999 |
| WO | 00/39318 | 7/2000 |
| WO | 00/61772 | 10/2000 |
| WO | 02/20721 | 3/2002 |
| WO | 03/023026 A | 3/2003 |
| WO | 2004/085660 | 10/2004 |

OTHER PUBLICATIONS

Barouch et al. (2000) "Augmentation of Immune Responses to HIV-1 and Simian Immunodeficiency Virus DNA Vaccines by IL-2/Ig Plasmid Administration in Rhesus Monkeys," Proc. Natl. Acad. Sci. USA 97(8):4192-4197.

Barry et al. (2004) "Expression library immunization to discover and improve vaccine antigens"; *Immunological Reviews* 199:68-83.

Bell et al. (Mar. 1978) "Effect of Low-NaCl Medium on the Envelope Glycoproteins of Sindbis Virus"; *J. Virol.* 25(3):764-769.

Berglund et al. (1993) "Semliki Forest Virus Expression System: Production of Conditionally Infectious Recombinant Particles," Bio/Technology 11:916-920.

Bergman et al. (Apr. 2003) "Long-Term Survival of Dogs with Advanced Malignant Melanoma after DNA Vaccination with Xenogeneic Human Tyrosinase: A Phase I Trial"; *Clin. Cancer Research* 9:1284-1290.

Betts et al. (1997) "Cross-Clade Human Immunodeficiency Virus (HIV)-Specific Cytotoxic T-Lymphocyte Responses in HIV-Infected Zambians," *J. Virol.* 71(11):8908-8911.

Bredenbeek et al. (1993) "Sindbis Virus Expression Vectors: Packaging of RNA Replicons by Using Defective Helper RNAs," J. Virol. 67:6439-6446.

Caley et al. (1997) "Humoral, Mucosal, and Cellular Immunity in Response to a Human Immunodeficiency Virus Type 1 Immunogen Expressed by a Venezuelan Equine Encephalitis Virus Vaccine Vector," J. Virol. 71(4):3031-3038.

Caley et al. (1999) "Venezuelan Equine Encephalitis Virus Vectors Expressing HIV-1 Proteins: Vector Design Strategies for Improved Vaccine Efficacy," Vaccine 17:3124-3135.

Casimiro et al. (Jan. 2002) "Vaccine-induced immune responses in rodents and nonhuman primates by use of a humanized immunodeficiency virus type 1 pol gene"; *J. Virol.* 76:185-195.

Chappell et al. (Feb. 2000) "A 9-nt Segment of a Cellular mRNA can Function as an Internal Ribosome Site (IRES) and When Present in Linked Vaccine Efficacy," Proc. Natl. Acad. Sci. USA 97(4):1536-1541.

Corsini et al. (1996) "Efficiency of Transduction by Recombinant Sindbis Replicon Virus Varies Among Cell Lines, Including Mosquito Cells and Rat Sensory Neurons," BioTechniques 21(3):492-497.

Cutler et al. (1986) "Mutants of the Membrane-binding Region of Semliki Forest Virus E2 Protein.l. Cell Surface Transport and Fusogenic Activity," J. Cell Biol. 102:889-901.

Davis et al. (1989) "In Vitro Synthesis of Infectious Venezuelan Equine Encephalitis Virus RNA from a cDNA Clone: Analysis of a Viable Deletion Mutant," Virol. 171:189-204.

Davis et al. (1990) "In Vitro Synthesis of Infectious Venezuelan Equine Encephalitis Virus RNS from a cDNA Clone: Analysis of a Viable Deletion Mutant and Mutations Affecting Virulence," *Vaccines* 90:109-113.

Davis et al. (1991) "Attenuating Mutations in the E2 Glycoprotein Gene of Venezuelan Equine Encephalitis Virus: Construction of Single and Multiple Mutants in a Full-Length cDNA Clone," Virol. 183:20-31.

Davis et al. (1993) "A Genetically Engineered Live Virus Vaccine for Venezuelan Equine Encephalitis," J. Cell Biochem. Supp O No. 17 part D, Abstract N404.

Davis et al. (1994) "A Molecular Genetic Approach to the Study of Venezuelan Equine Encephalitis Virus Pathogenesis," Arch. Virol. 9:99-109.

Davis et al. (1995) "Attenuated Mutants of Venezuelan Equine Encephalitis Virus Containing Lethal Mutations in the PE2 Cleavage Signal Combined with a Second-Site Suppressor Mutation in E1," Virol. 212:102-110.

Davis et al. (1996) "A Viral Vaccine Vector that Expresses Foreign Genes in Lymph Nodes and Protects Against Mucosal Challenge," J. Virol. 70:3781-3787.

Davis et al. (1996) "Immunization Against Influenza with Attenuated Venezuelan Equine Encephalitis Virus Vectors," In: Options for the Control of Influenza III, L.E.Brown and A.W.Hampson, eds. Elsevier, Amsterdam pp. 803-809.

Davis et al. (2001) "Vaccination of Macaques Against Pathogenic Simian Immunodeficiency Virus with Venezuelan Equine Encephalitis Virus Replicon Particles," J. Virol. 74(1):371-378.

Davis N.L., et al. (Apr. 2002) "Alphavirus Replicon 16-20 Particles as Candidate HIV Vaccines," IUBMB Life, Taylor and Francis, London, 53(4-5):209-211.

Dubensky et al. (1996) "Sindbis Virus DNA-Based Expression Vectors: Utility for in Vitro and in Vivo Gene Transfer," J. Virol. 70:508-519.

Dubuisson et al. (1993) "Sindbis Virus Attachment: Isolation and Characterization of Mutants With Impaired Binding to Vertebrate Cells," J. Virol. 67:3363-3374.

Favre et al. (1993) "Semliki Forest Virus Capsid Protein Expressed by a Baculovirus Recombinant," Arch. Virol. 132:307-319.

Feyzi et al (1997) "Structural Requirement of Heparan Sulfate for Interaction with Herpes Simplex Virus Type 1 Virions and Isolated Glycoprotein C," J. Biol. Chem. 272(40):24850-24857.

Frolov et al. (1996) "Alphavirus-based expression vectors: Strategies and applications"; *Proc. Natl. Acad. Sci. USA* 93:11371-11377.

Garoff et al. (1983) "Expression of Semliki Forest Virus Proteins from Cloned Complementary DNA. II. The Membrane-Spanning Glycoprotein E2 is Transported to the Cell Surface Without its Normal Cytoplasmic Domain," J. Cell Biol. 97:652-658.

Geigenmuller-Gnirke et al. (1991) "Complementation Between Sindbis Viral RNAs Produce Infectious Particles with a Bipartite Genome," Proc. Natl. Acad. Sci. USA. 88:3253-3257.

Geisbert et al. (May 2002) "Evaluation in Nonhuman Primates of Vaccines against Ebola Virus"; *Emerging Infect. Dis.* 8(5):503-507.

(56) References Cited

OTHER PUBLICATIONS

Gingras et al. (1996) "Activation of the Translational Suppressor 4E-BP1 Following Infection with Encephalomyocarditis Virus and Poliovirus," Proc. Natl. Acad. Sci. USA 93:5578-5583.

Gradi et al. (1998) "Proteolysis of Human Eukaryotic Translation Initiation Factor eIF4GII, but Not eIF4GI, Coincides with the Shutoff of Host Protein Synthesis after Poliovirus Infection," Proc. Natl. Acad. Sci. USA 95:11089-11094.

Grieder et al. (1995) "Specific Restrictions in the Progression of Venezuelan Equine Encephalitis Virus-Induced Disease Resulting from Single Amino Acid Changes in Glycoproteins," Virol. 206:994-1006.

Hahn et al. (1992) "Infectious Sindbis Virus Transient Expression Vectors for Studying Antigen Processing and Presentation," *Proc. Natl. Acad. Sci. USA* 89:2679-2683.

Heidner et al. (1994) "Lethality of PE2 Incorporation into Sindbis Virus can be Suppressed by Second-Site Mutations in E3 and E2," J. Virol. 68:2683-2692.

Heise et al. (Jan. 2003) "An Attenuation Mutation in nsP1 of the Sindbis-Group Virus S.A.AR86 Accelerates Nonstructural Protein Processing and Up Regulates Viral 26S RNA Synthesis," J. Virol. 77(2):1149-1156.

Heiser et al. (Feb. 2002) "Autologous Dendritic Cells Transfected with Prostate-Specific Antigen RNA Stimulate CTL Responses Against Metastatic Prostate Tumors," *J. Clin. Inv.* 109(3):409-417.

Herweijer et al. (1997) "Self-Amplifying Vectors for Gene Delivery," Adv. Drug Rev. 27:5-16.

Hevey et al. (1998) "Marburg Virus Vaccines Based upon Alphavirus Replicons Protect Guinea Pigs and Nonhuman Primates"; *Virology* 251:28-37.

Hevey et al. (Nov. 2001) "Marburg Virus Vaccines: Comparing Classical and New Approaches," Vaccine 20:586-593.

Hirsch et al. (1996) "Patterns of Viral Replication Correlate with Outcome in Simian Immunodeficiency Virus (SIV)-Infected Macaques: Effect of Prior Immunization with a Trivalent SIV Vaccine in Modified Vaccinia Virus Ankara," J. Virol. 70(6):3741-3752.

Hodgson et al. (1993) "Expression of Venezuelan Equine Encephalitis Viral Proteins by Recombinant Baculoviruses," Am. J. Trop. Med. Hygiene 49:195-196.

Holcik et al. (1999) "A New Internal-Ribosome-Entry-Site Motif Potentiates XIAP-Mediated Cytoprotection," Nature Cell Biol. 1:190-192.

Holcik et al. (2000) "Functional Characterization of the X-Linked Inhibitor of Apoptosis (XIAP) Internal Ribosome Entry Site Element: Role of La Autoantigen in XIAP Translation," Mol. Cell. Biol. 20(13):4648-4657.

Holcik et al. (Jan. 2003) "The Internal Ribosome Entry Site-Mediated Translation of Antiapoptotic Protein XIAP is Modulated by the Heterogeneous Nuclear Ribonucleoproteins C1 and C2," Mol. Cell. Biol. 23(1):280-288.

Jalanko (1985) "Expression of Semliki Forest Virus Capsid Protein from SV40 Recombinant Virus," FEBS Lett. 186:59-64.

Jang et al. (1990) "Cap-Independent Translation of Encephalomyocarditis Virus RNA: Structural Elements of the Internal Ribosomal Entry Site and Involvement of a Cellular 57kD RNA-Binding Protein," Genes and Development 4:1560-1572.

Joachims et al. (1999) "Cleavage of Poly(A)-Binding Protein by Enterovirus Proteases Concurrent with Inhibition of Translation In Vitro," J. Virol. 73(1):718-727.

Johnston et al. (1988) "Selection for Accelerated Penetration in Cell Culture Coselects for Attenuated Mutants of Venezuelan Equine Encephalitis Virus," Virol. 162:437-443.

Johnston et al. (1996) "Alphaviruses,", In: Fields Virology, 3rd ed., Lippincott-Raven Publishers, Philadelphia, Chapt 28:843-898.

Kinney et al. (1989) The Full-Length Nucleotide Sequences of the Virulent Trinidad Donkey Strain of Venezuelan Equine Encephalitis Virus and Its Attenuated Vaccine Derivative, Strain TC-83, *Virology* 170:19-30.

Kinney et al. (1993) "Attenuation of Venezuelan Equine Encephalitis Virus Strain TC-83 Is Encoded by the 5'-Noncoding Region and the E2 Envelope Glycoprotein," J. Virol. 67:1269-1277.

Knight (1999) "Secretion from Bovine Chromaffin Cells Acutely Expressing Exogenous Proteins using a Recombinant Semliki Forest Virus Containing an EGFP Reporter," Mol. Cell. Neuro. 14(6):486-505.

Kohl et al. (1999) "Transient Gene Expression in Mammalian and Mosquito Cells Using a Recombinant Semliki Forest Virus Expressing T7 RNA Polymerase," Appl. Microbiol. Biotechnol. 53(1):51-56.

Koller et al. (Sep. 2001) "A high-throughput alphavirus-based expression cloning system for mammalian cells"; *Nature Biotech.* 19:851-855.

Kondor-Koch et al. (1983) "Expression of Semliki Forest Virus Proteins from Cloned Complementary DNA. I. The Fusion Activity of the Spike Glycoprotein," J. Cell. Biol. 97(3):644-651.

Kumamoto et al. (Jan. 2002) "Induction of Tumor-Specific Protective Immunity by in situ Langerhans Cell Vaccine," Nature *Biotech.* 20:64-69.

Lee et al. (1997) "Efficient Long-Term Coexpression of a Hammerhead Ribozyme Targeted to the U5 Region of HIV-1 LTR by Linkage to the Multidrug-Resistance Gene," Antisense & Nucleic Acid Drug Development 7:511-522.

Leitner et al. (Jan. 2000) "Enhancement of Tumor-specific Immune Response with Plasmid DNA Replicon Vectors"; *Cancer Research* 60:51-55.

Lemm et al. (1994) "Polypeptide Requirements for Assembly of Functional Sindbis Virus Replication Complexes: A Model for the Temporal Regulation of Minus-and Plus-Strand RNA Synthesis," *EMBO J.* 13:2925-2934.

Leone et al. (1985) "In Vitro Synthesis of the Gene Coding for the Glycoprotein E1 of Sindbis Virus," Microbiologica 8(2):123-130.

Li et al. (1996) "Production of Infectious Recombinant Moloney Murine Leukemia Virus Particles in BHK Cells Using Semliki Forest Virus-Derived RNA Expression Vectors," Proc. Natl. Acad. Sci. USA 93:11658-11663.

Li et al. (Oct. 1996) "Production of infectious recombinant Moloney murine leukemia virus particles in BHK cells using Semliki Forest virus-derived RNA expression vectors." *Proc. Natl. Acad. Sci. USA.* 93:11658-11663.

Liljestrom (1994) "Alphavirus Expression Systems," Curr. Opin. Biotechnol. 5:495-500.

Liljestrom et al. (1991) "A New Generation of Animal Cell Expression Vectors Based on the Semliki Forest Virus Replicon." BioTechnology 9:1356-1361.

Lobigs et al. (1990) "Fusion Function of the Semliki Forest Virus Spike is Activated by Proteolyic Cleavage of the Envelope Glycoprotein Precursor p62," J. Virol. 64:1233-1240.

Ludwig G.V., et al. (1996) "A Putative Receptor for Venezuelan Equine Encephalitis Virus from Mosquito Cells," Journal of Virology, 70(8):5592-5599.

Lundstrom et al. (1985) "Secretion of Semliki Forest Virus Membrane Glycoprotein E1 from *Bacillus subtilis*," Virus Res. 2:69-83.

Martinez-Salas et al. (May 2001) "Functional Interactions in Internal Translation Initiation Directed by Viral and Cellular IRES Elements," J. Gen. Virol. 82:973-984.

McKnight et al. (1996) "Deduced Consensus Sequence of Sindbis Virus Strain AR339: Mutations Contained in Laboratory Strains which Affect Cell Culture and In Vivo Phenotypes," J. Virol. 70(3):1981-1989.

Melancon et al. (1986) "Reinitiation of Translocation in the Semliki Forest Virus Structural Polyprotein: Identification of the Signal for the E1 Glycoprotein," EMBO J. 5:1551-1560.

Melancon et al. (1987) "Processing of the Semliki Forest Virus Structural Polyprotein: Role of Capsid Protease," J. Virol. 61:1301-1309.

Morgenstern et al. (1990) "Advanced Mammalian Gene Transfer: High Titre Retroviral Vectors with Multiple Drug Selection Markers and a Complementary Helper-Free Packaging Cell Line," Nuc. Acid. Res. 18:3587-3596.

Nestle et al. (1998) "Vaccination of Melanoma Patients with Peptide or Tumor Lysate-Pulsed Dendritic Cells." *Nature Medicine.* 4(3):328-332 (Abstract Only).

(56) References Cited

OTHER PUBLICATIONS

Oker-Blom et al. (1989) "Expression of Sindbis Virus 26S cDNA in *Spodoptera frugiperda* (Sf9) Cells, Using a Baculovirus Expression Vector," J. Virol. 63:1256-1264.

Orkin et al. (1995) "Report and Recommendations of the Panel to Assess the NIH Investment in Research on Gene Therapy".

Overwijk et al. (Jan. 2001) "Creating therapeutic cancer vaccines: notes from the battlefield"; *Trends in Immunol.* 22(1):5-7.

Pardoll, D.M. (Apr. 2002) Spinning Molecular Immunology into Successful Immunotherapy; *Nature Reviews—Immunology* 2:227-238.

Pardoll, D.M. (May 1998) "Cancer Vaccines"; *Nature Medicine Vaccine Supplement* 4(5):525-531.

Paredes et al. (1993) "Three-Dimensional Structure of a Membrane-Containing Virus," Proc. Natl. Acad. Sci. USA 90:9095-9099.

Pierce, J.S., et al. (1974) "Effect of Ionic Strength on the Binding of Sindbis Virus to Chick Cells," Journal of Virology, 13(5):1030-1036.

Polo et al. (1990) "Attenuating Mutations in Glycoproteins E1 and E2 of Sindbis Virus Produces a Highly Attenuated Strain When Combined in Vitro," J. Virol. 64:4438-4444.

Presley et al. (1991) "Proteolytic Processing of the Sindbis Virus Membrane Protein Precursor PE2 is Nonessential for Growth in Vertebrate Cells but is required for Efficient Growth in Invertebrate Cells," J. Virol. 65:1905-1909.

Pugachev et al. (2000) "Development of a Rubella Virus Vaccine Expression Vector: Use of a Picornavirus Internal Ribosome Entry Site Increases Stability of Expression," J. Virol. 74:10811-10815.

Pushko et al. (1997) "Replicon-Helper systems from Attenuated Venezuelan Equine Encephalitis Virus: Expression of Heterologous Genes in Vitro and Immunization against Heterologous Pathogens in Vivo"; Virology 239:389-401.

Pushko et al. (1997) "Replicon-Helper Systems from Attenuated Venezuelan Equine Encephalitis Virus: Expression of Heterologous Genes in Vitro and Immunization Against Heterologous Pathogens in Vivo," Virol. 239:389-401.

Pushko et al. (Dec. 2001) "Individual and Bivalent Vaccines Based on Alphavirus Replicons Protect Guinea Pigs Against Infection with Lassa and Ebola Viruses," J. Virol. 75(23):11677-11685.

Ragupathi et al. (Aug. 2002) "The case for polyvalent cancer vaccines that induce antibodies"; *Expert Rev. Vaccines* 1(2):193-206.

Rayner et al. (Sep.-Oct. 2002) "Alphavirus Vectors and Vaccination," Rev. Med. Virol. 12:279-296.

Rayner et al. (Sep. 2002) "Alphavirus Vectors and Vaccination," Rev. Med. Virol. 12(5):279-296.

Rice et al. (1985) "Expression of Sindbis Virus Structural Proteins via Recombinant Vaccinia Virus: Synthesis, Processing, and Incorporation into Mature Sindbis Virions," J. Virol. 56:227-239.

Riedel (1985) "Different Membrane Anchors Allow the Semliki Forest Virus Spike Subunit E2 to Reach the Cell Surface," J. Virol. 54:224-228.

Roberts et al. (1997) "Complementation of Defective Picornavirus Internal Ribosome Entry Site (IRES) Elements by the Coexpression of Fragments of the IRES," Virol. 227:53-62.

Russell et al. (1989) "Sindbis Virus Mutations Which Coordinately Affect Glycoprotein Processing, Penetration, and Virulence in Mice," J. Virol. 63:1619-1629.

Sadanaga et al. (Aug. 2001) "Dendritic cell vaccination with MAGE peptide is a novel therapeutic approach for gastrointestinal carcincomas"; Clin. Cancer Res. 7:2277-2284.

Salminen et al. (1992) "Membrane Fusion Process of Semliki Forest Virus II: Cleavage-Dependant Reorganization of the Spike Protein Complex Controls Virus Entry," J. Cell. Biol. 116:349-357.

Schlesinger et al. (1994) "Recombination Between Sindbis Virus RNAs," J. Virol. 65:4017-4025.

Schlesinger et al. (1996) "Togaviridae:The Viruses and Their Replication," In: Fields Virology, 3rd Edition, Lipincott-Raven Publishers, Philadelphia, pp. 825-841.

Schoepp et al. (1993) "Directed Mutagenesis of a Sindbis Virus Pathogenesis Site," Virol. 193:149-159.

Shi et al. (May 2002) "Construction and Characterization of Subgenomic Replicons of New York Strain of West Nile Virus," Virol. 296(2):219-233.

Simpson et al. (1996) "Complete Nucleotide Sequence and Full Length cDNA Clone of S.A.Ar86, a South African Alphavirus Related to Sindbis," Virol. 222:464-469.

Sjoberg et al. (1994) "A Significantly Improved Semliki Forest Virus Expression System Based on Translation Enhancer Segments from the Viral Capsid Gene," BioTechnol. 12:1127-1131.

Slepushkin et al. (Sep.-Oct. 2003) "Large scale purification of a lentiviral vector by size exclusion chromatography or mustang Q ion exchange capsule."; *Bioprocessing J.* p. 89-94.

Slovin et al. (1999) "Carbohydrate Vaccines in Cancer: Immunogenicity of a Fully Synthetic Globo H Hexasaccharide Conjugate in Man." *Proc Natl Acad Sci*. 5710-5715.

Smooker et al. (2000) "Expression Library Immunization Protects Mice Against a Challenge with Virulent Rodent Malaria." *Vaccine*. 18: 2533-2540.

Strauss et al. (1990) "Alphavirus Proteinases," Sem. Virol. 1:347-356.

Strauss et al. (1994) "The Alphaviruses: Gene Expression, Replication, and Evolution," Microbiological Rev. 58:491-562.

Suomalainen et al. (1992) "Spike Protein-Nucleocapsid Interactions Drive the Budding of Alphaviruses," J. Virol. 66(8):4737-4747.

Sykes et al. (1999) "Genetic Live Vaccines Mimic the Antigenicity but Not Pathogenicity of Live Viruses," DNA Cell Biol. 18(7):521-531.

Thompson et al. (Oct. 2003) "Enterovirus 71 Contains a Type I IRES Element that Functions When Eukaryotic Initiation Factor eIF4G is Cleaved," Virol. 315:259-266.

Ubol et al. (1994) "Neurovirulent Strains of Alphavirus Induce Apoptosis in bcl-2-Expressing Cells: Role of a Single Amino Acid Change in the E2 Glycoprotein," Proc. Natl. Acad. Sci. USA 91:5202-5206.

Van der Velden et al. (1995) "Defective Point Mutants of the Encephalomyocarditis Virus Internal Ribosome Entry Site can be Complemented in Trans," Virol. 214:82-90.

Verma et al. (1997) "Gene Therapy—Promise and Prospects," Nature 389:239-242.

Waite et al. (Jan. 1970) "Inhibition of Sindbis Virus Production by Media of Low Ionic Strength: Intracellular Events and Requirements for Reversal"; *J. Virol.* 5:60-71.

Wang et al. (2000) "Core Protein-Coding Sequence, But Not Core Protein, Modulates the Efficiency of Cap-Independent Translation Directed by the Internal Ribosome Entry Site of Hepatitis C Virus," J. Virol. 74(23):11347-11358.

Ward et al. (Sep. 2002) "Immunotherapeutic Potential of Whole Tumor Cells," *Cancer Immunol. Immunother*. 51:351-357.

Weiss et al. (1991) "Recombination Between Sindbis Virus RNAs," J. Virol. 65:4017-4025.

Wen et al. (1986) "Expression of Genes Encoding Vesicular Stomatitis and Sindbis Virus Glycoproteins in Yeast Leads to Formation of Disulfide-Linked Oligomers," Virol. 153:150-154.

Wen et al. (2001) "Tricistronic Viral Vectors Co-Expressing Interleukin-12 (IL-12) and CD80 (B7-1) for the Immunotherapy of Cancer: Preclinical Studies in Myeloma," Cancer Gene Therapy 8(5):361-370.

Williamson et al. (Feb. 2003) "Characterization and Selection of HIV-1 Subtype C Isolates for Use in Vaccine Development," Aids Research and Human Retroviruses 19(2):133-144.

Wilson et al. (2000) "Naturally Occurring Dicistronic Cricket Paralysis Virus RNA is Regulated by Two Internal Ribosome Entry Sites," Mol. Cell. Biol. 20(14):4990-4999.

Wilson et al. (Aug. 2001) "Vaccine Potential of Ebola Virus VP24, VP30, VP35, and VP40 Proteins"; *Virology* 286:384-390.

Xiong et al. (1989) "Sindbis Virus: An Efficient, Broad Host Range Vector for Gene Expression in Animal Cells," Science 243:1188-1191.

Yamanaka et al. (Mar. 2001) "Enhancement of antitumor immune response in glioma models in mice by genetically modified dendritic cells pulsed with Semliki Forest virus-mediated complementary DNA"; *J. Neurosurg*. 94:474-481.

(56) References Cited

OTHER PUBLICATIONS

Yamanaka et al. (Sep. 2002) "Marked enhancement of antitumor immune responses in mouse brain tumor models by genetically modified dendritic cells producing Semliki Forest virus-mediated interleukin-12"; *J. Neurosurg.* 97:611-618.
Yang et al. (1997) "Location of the Internal Ribosome Entry Site in the 5'Non-Coding Region of the Immunoglobulin Heavy-Chain Binding Protein (BiP) mRNA: Evidence for Specific RNA-Protein Interactions," Nuc. Acids. Res. 25(14):2800-2807.
Ying et al. (1999) "Cancer therapy using a self-replicating RNA vaccine"; *Nature Medicine* 5(7):823-827.
Zhao et al. (1992) "Role of Cell Surface Spikes in Alphavirus Budding," J. Virol. 66:7089-7095.
File History for US Patent 7,078,218, to smith et al., Jul. 18, 2006.
File History for U.S. Appl. No. 10/735,601 from which present application takes priority, Smith et al.
Anderson et al. (Jul./Aug. 2001) "Comparative Immunization Study Using RNA and DNA Constructs Encoding a Part of the *Plasmodium falciparum* Antigen Pf332," *Scand. J. lmmunol.* 54(1):117-124.
Cheng et al. (May 2001) "Enhancement of Sindbis Virus Self-Replicating RNA Vaccine Potency by Linkage of *Mycobacterium tuberculosis* Heat Shock Protein 70 Gene to an Antigen Gene," *J. lmmunol.* 166:6218-6226.
Shultz-Cherry et al. (Dec. 5, 2000) "Influenza Virus (A/HK/156/97) Hemagglutinin Expressed by an Alphavirus Replicon System Protects Chickens Against Lethal Infection with Hon Kong-Origin H5N1 Viruses," *Virology* 278(1):55-59.
AU First Office Action, dated Jun. 24, 2008, in Australian Patent Application No. 115183, a related application, 2 pp.
Response to First AU Office Action, dated Nov. 5, 2008, in Australian Patent Application No. 115183, a related application, 16 pp.
AU Second Office Action, dated Nov. 12, 2008, in Australian Patent Application No. 115183, a related application, 2 pp.
Response to Second AU Office Action, dated Feb. 10, 2009, in Australian Patent Application No. 115183, a related application, 26 pp.
CA First Office Action, dated Nov. 1, 2010, in Canadian Patent Application No. 2,509,973, a related application, 4 pp.
Response to First CA Office Action, dated May 2, 2011, in Canadian Patent Application No. 2,509,973, a related application, 13 pp.
CA Second Office Action, dated Aug. 18, 2011, in Canadian Patent Application No. 2,509,973, a related application, 2 pp.
Response to Second CA Office Action, dated Feb. 14, 2012, in Canadian Patent Application No. 2,509,973, a related application, 6 pp.
EP Supplemental Search Report, dated Apr. 2, 2007, in European Patent Application No. 03813432.6, a related application, 3 pp.
EP First Office Action, dated Jul. 10, 2007, in European Patent Application No. 03813432.6, a related application, 2 pp.
Response to First EP Office Action, dated Dec. 6, 2007, in European Patent Application No. 03813432.6, a related application, 7 pp.
JP First Office Action, dated Aug. 11, 2009, in Japanese Patent Application No. 2004-560854, a related application, 6 pp.
JP Second Office Action, dated Dec. 7, 2010, in Japanese Patent Application No. 2004-560854, a related application, 6 pp.
JP Third Office Action, dated Dec. 13, 2011, in Japanese Patent Application No. 2004-560854, a related application, 3 pp.
Bernard et al. (2000) "Mutations in the E2 Glycoprotein of Venezuelan Equine Encephalitis Virus Confer Heparan Sulfate Interaction, Low Morbidity, and Rapid Clearance from Blood of Mice," Virology 278:93-103.
Gold et al. (2003) "A Single Heteroclitic Epitope Determines Cancer Immunity After Xenogeneic DNA Immunization Against a Tumor Differentiation Antigen," Journal of Immunology 170:5188-5194.
Waite et al. (Sep. 1972) "Inhibition of Sindbis Virus Release by Media of Low Ionic Strength: an Electron Microscope Study," J. Virol. 10(3):537-544.
Supplemental European Search Report, dated Apr. 2, 2007, in European Patent Application No. 03813432.6, a corresponding application, 3 pp.
EP First Office Action, dated Jun. 4, 2007, in European Patent Application No. 03813432.6, a corresponding application, 9 pp.
First European Office Action response, dated Dec. 6, 2007, in European Application No. 03813432.6, a corresponding application, 11 pp.
EP Second Office Action, dated Jul. 4, 2012, in European Patent Application No. 03813432.6, a corresponding application, 7 pp.
Second European Office Action response, dated Nov. 14, 2012, in European Application No. 03813432.6, a corresponding application, 4 pp.
Third EP First Office Action, dated Jan. 18, 2013, in European Patent Application No. 03813432.6, a corresponding application, 6 pp.
Search Report, dated Aug. 17, 2004, corresponding to International Application No. PCT/US03/39723 (filed Dec. 12, 2003), a corresponding application, 4 pp.
Search Report, dated Dec. 3, 2004, corresponding to International Application No. PCT/US03/39725 (filed Dec. 12, 2003), application with related technology and inventor in common of the present application, 6 pp.

* cited by examiner

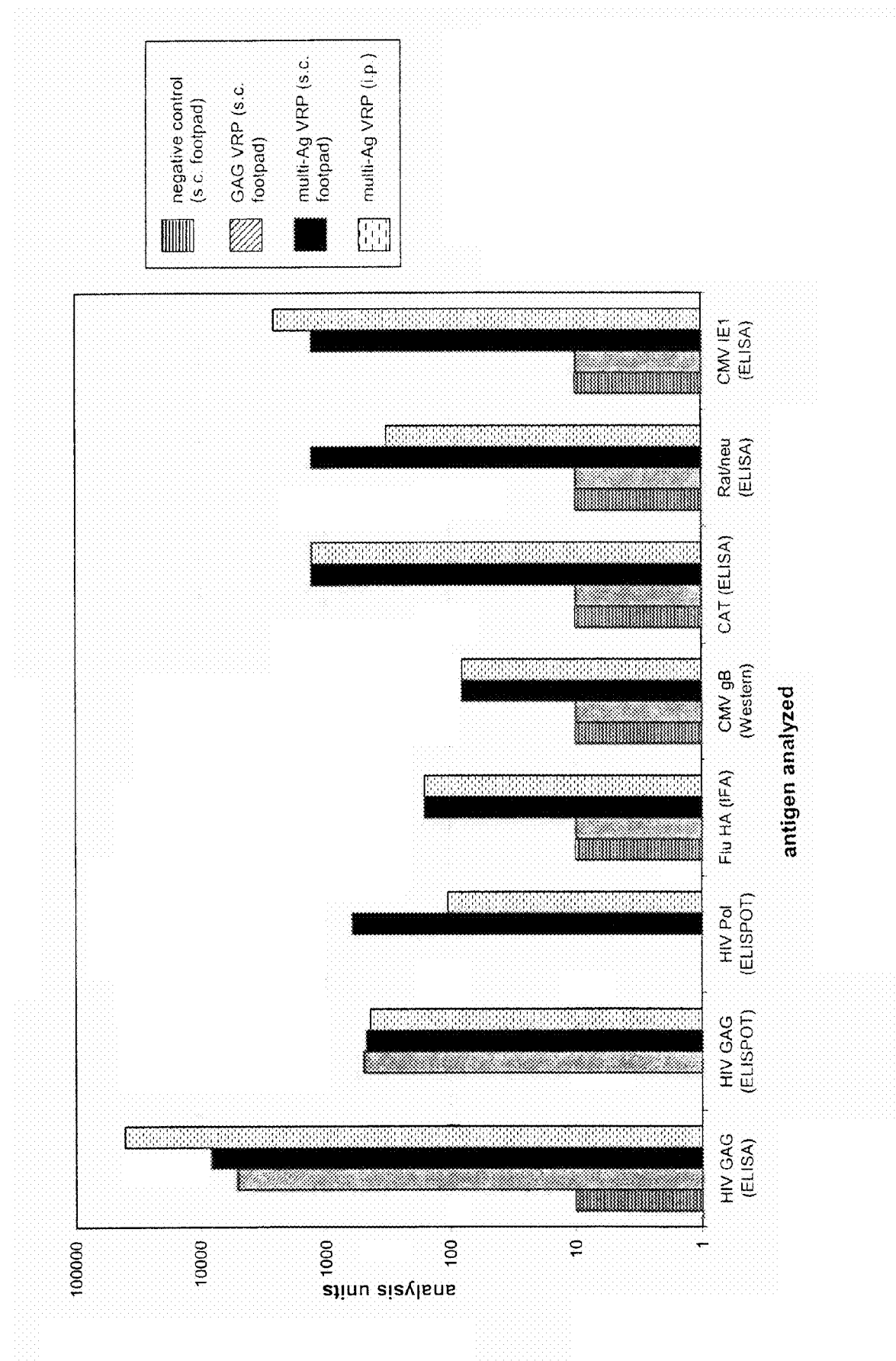

```
SEQUENCE LISTING

<160> NUMBER OF SEQ ID NOS: 3

<210> SEQ ID NO 1
<211> LENGTH: 11
<212> TYPE: PRT
<213> ORGANISM: Artificial
<220> FEATURE:
<223> OTHER INFORMATION: peptide epitope of murine Pol CTL

<400> SEQUENCE: 1

Val Tyr Tyr Asp Pro Ser Lys Asp Leu Ile Ala
1               5                   10

<210> SEQ ID NO 2
<211> LENGTH: 11
<212> TYPE: PRT
<213> ORGANISM: Artificial
<220> FEATURE:
<223> OTHER INFORMATION: peptide epitople of murine Pol CTL

<400> SEQUENCE: 2

Glu Leu Arg Gln His Leu Leu Arg Trp Gly Leu
1               5                   10

<210> SEQ ID NO 3
<211> LENGTH: 11
<212> TYPE: PRT
<213> ORGANISM: Artificial
<220> FEATURE:
<223> OTHER INFORMATION: peptide epitope of murine Pol CTL

<400> SEQUENCE: 3

Glu Leu Arg Glu His Leu Leu Lys Trp Gly Phe
1               5                   10
```

MULTI-ANTIGENIC ALPHAVIRUS REPLICON PARTICLES AND METHODS

CROSS REFERENCE TO RELATED APPLICATIONS

This application is a Divisional Application of U.S. application Ser. No. 10/735,601, filed Dec. 12, 2003, now abandoned, which application claims benefit of U.S. Provisional Application Nos. 60/433,299 and 60/433,058, both filed Dec. 13, 2002; all incorporated to the extent there is no inconsistency herewith.

ACKNOWLEDGMENT OF FEDERAL RESEARCH SUPPORT

Not applicable.

BACKGROUND OF THE INVENTION

The present invention relates to recombinant DNA technology, and in particular to introducing foreign nucleic acid (s) into a eukaryotic host cell, and more particularly to producing infective, propagation-defective virus-like particles which collectively direct the expression of a representative set of immunogenic proteins (an expression library) of a pathogen (virus, fungus, bacterium or protozoan), parasite or tumor cell. These libraries have applications in human and veterinary medicine.

A vaccine is one of the most efficacious, safe and economical strategies for preventing disease and controlling the spread of disease. Conventional vaccines are a form of immunoprophylaxis given before disease occurrence to afford immunoprotection by generating a strong host immunological memory against a specific antigen. The primary aim of vaccination is to activate the adaptive specific immune response, primarily to generate B and T lymphocytes against specific antigen(s) associated with the disease or the disease agent.

Similarly, cancer vaccines aim to generate immune responses against cancer tumor-associated antigens. Cancers can be immunogenic and can activate host immune responses capable of controlling the disease and causing tumor regression. However, cancer at the same time can be specifically and nonspecifically immunosuppressive and can evade the host's immune system. Many protein/glycoprotein tumor-associated antigens have been identified and linked to certain types of cancer. Her-2-neu, PSA, PSMA, MAGE-3, MAGE-1, gp100, TRP-2, tyrosinase, MART-1, β-HCG, CEA, Ras; B-catenin, gp43, GAGE-1, BAGE-1, MUC-1,2,3, and HSP-70 are just a few examples.

Multiple approaches are being assessed in immunizing cancer patients with tumor-associated antigens (TAAs). Vaccines in clinical use fall into several categories determined by their components, which range from whole cells to immunogenic peptides. Whole cell and cell lysate vaccines can be autologous or allogeneic vaccines, depending on the host origin of the cancer cells. An autologous whole cell cancer vaccine is a patient-specific formulation made from the patient's own tumor. To date, many autologous cancer vaccines have not been clinically successful unless they are modified to increase their intrinsic immunogenicity, for example by the co-expression of lymphokines such as GM-CSF (Ward et. al., 2002. *Cancer Immunol. Immunother.* 51:351-7). Because they are patient-specific, they can also be costly and limited to those patients from whom cancer cells can be obtained in sufficient quantity to produce a single-cell suspension. In addition, the inherently limited number of cells is problematic with respect to the need for modification or for multiple vaccinations, making an autologous formulation impractical for prophylaxis or treatment of early disease. Some of these problems are solved with allogeneic whole cell vaccines or genetically engineered whole cell vaccines where instead of supplying immunostimulatory agents such as lymphokines exogenously with the tumor vaccine, the tumor cells are genetically modified to express the lymphokine endogenously. However, these methods may be time consuming and prohibitively expensive to produce.

Natural and recombinant cancer protein antigen vaccines are subunit vaccines. Unlike whole cell vaccines, these subunit vaccines contain defined immunogenic antigens at standardized levels. The key problem with such vaccines is finding the right adjuvant and delivery system. In addition, purification of natural or recombinant tumor antigens is tedious and not always logistically practical. Protein cancer vaccines require culturing tumor cells, purifying tumor antigens, or producing specific peptides or recombinant proteins. In addition, vaccines that are made solely from tumor protein/ peptides pose intrinsic problems in that they can be limited in the ability to be directed into the correct antigen presentation pathways or may not be recognized by the host due to host major histocompatibility complex (MHC) polymorphisms. For these reasons, whole cell, or vector delivered tumor vaccines expressing a large array of tumor antigens are anticipated to be preferred vaccination methods. Vaccines which include nucleic acid encoding the tumor antigens rather than vaccines comprising the antigen itself, address some of these problems. To date these approaches have shown the most promise in pre-clinical and clinical testing. Amongst the current technologies being applied to cancer vaccination, two particular systems have shown significant potential for application in this field. The first is delivery of TAAs using viral vectors, including but not limited to adenoviral, adeno associated virus, retroviral, poxviruses, flaviviruses, picornaviruses, herpesviruses and alphaviruses (see WO 99/51263). The second is vaccination with tumor cell protein or RNA using ex vivo derived dendritic cells as the delivery vehicle for transfer and expression of the TAAs into the host (Heiser et al., 2002. J. Clin. Inv. 109:409-417 and Kumamoto et al., 2002. Nature Biotech. 20:64-69).

A limiting factor in many tumor vaccine approaches appears to be the limited availability of known tumor-specific antigens. These tumor-specific antigens can vary not only between tissue type from which the tumor originated, but may even vary from cell-to-cell within the same tumor. A confounding problem associated with using only a limited number of tumor antigen targets in a vaccine is the potential for "tumor escape" where the tumor essentially evades detection by the vaccine induced immune effector cells by deleting certain tumor associated antigens.

This observation prompted investigators to design cancer vaccines expressing multiple antigens to reduce the propensity of tumor escape. Unfortunately due to the limited number of antigens that have been identified to date, this is not a feasible approach for the majority of tumors. Therefore, a more recent evolution of cancer therapy has been the use of entire tumor antigen libraries. This combines multiple beneficial characteristics one would want in a cancer vaccine. A vaccine encoding an entire tumor antigen repertoire negates the need for antigen identification and isolation; essentially the vaccine recipient's immune system is allowed to make this choice in determining which TAAs the individual will respond to. The second distinct advantage of this approach is that, since the repertoire of antigens being expressed is so broad, the chance of tumor escape is minimized or eliminated entirely. Currently this approach is most actively being pursued using dendritic cells to deliver tumor antigen libraries. These cells, which function as antigen presenting cells by presenting the tumor antigens to the immune system, are isolated from each cancer patient, cultured and expanded in vitro, loaded with tumor antigen either in the form of protein or nucleic acid; see U.S. Pat. Nos. 5,853,719 and 6,306,388. This approach has generated promising clinical data in human testing and has shown the ability to retard tumor growth in some individuals, and even to drive tumor regression in a number of patients (Sadanaga et. al., 2001, *Clin. Cancer Res.* 7:2277-84). The major drawback for this technology is the need for in vitro culture, expansion and antigen loading of the patient derived dendritic cells prior to vaccination of each individual. This is a time consuming and expensive process, and can be highly variable since the dendritic cell population from individual to individual can vary widely in its phenotype, growth characteristics and activity.

To date, naked DNA, RNA, viral and bacterial vectors have been tested for their ability to induce cancer specific responses against a tumor antigen library. An alternative approach is the use of viral vectors to deliver a tumor antigen library to a cancer patient. To date, some success has been achieved with naked nucleic acid expression libraries; e.g., see U.S. Pat. Nos. 5,989,553 and 5,703,057. Attempts to augment the immune responses elicited to naked nucleic acid vectors include the use of self-replicating viral vectors delivered in the form of naked RNA or DNA (Ying et al., 1999, *Nature Medicine*, 5:823-827).

Viral vectors have shown great promise in pre-clinical and clinical testing for prevention of a number of infectious disease targets. One of the most pressing issues for development of viral vectors for prophylactic and therapeutic vaccine uses in humans is the ability to produce enough particles in a regulatory acceptable form. For many viral systems, this goal is within reach and a number of vector systems have produced positive immune response and safety profiles in clinical trials. However, most production schemes for vaccine vector platforms are focused on production of large quantities of vaccine particles expressing single or at the most two or three known antigens for specific disease targets e.g. the gag, pol and env genes of HIV in poxvirus vectors. However, in most cases, these large-scale manufacturing approaches are not practical for the manufacture of individual patient-specific vaccines.

Alphaviral vector delivery systems have been identified as attractive vaccine vectors for a number of reasons including: high expression of heterologous gene sequences, the derivation of non-replicating (alpha)virus replicon particles (ARP) with good safety profiles, an RNA genome which replicates in the cytoplasm of the target cell and negates the chance of genomic integration of the vector, and finally the demonstration that certain alphaviral vectors are intrinsically targeted for replication in dendritic cells and thus can generate strong and comprehensive immune responses to a multitude of vaccine antigens (reviewed in Rayner, Dryga and Kamrud, 2002, *Rev. Med. Virol.* 12:279-296). The Alphavirus genus includes a variety of viruses, all of which are members of the Togaviridae family. The alphaviruses include Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J Virus, Fort Morgan Virus, Ndumu Virus, and Buggy Creek Virus. The viral genome is a single-stranded, messenger-sense RNA, modified at the 5'-end with a methylated cap and at the 3'-end with a variable-length poly (A) tract. Structural subunits containing a single viral protein, C, associated with the RNA genome in an icosahedral nucleocapsid. In the virion, the capsid is surrounded by a lipid envelope covered with a regular array of transmembrane protein spikes, each of which consists of a heterodimeric complex of two glycoproteins, usually E1 and E2. See Pedersen et al., *J. Virol* 14:40 (1974). The Sindbis and Semliki Forest viruses are considered the prototypical alphaviruses and have been studied extensively. See Schlesinger, The Togaviridae and Flaviviridae, Plenum Publishing Corp., New York (1986). The VEE virus has also been extensively studied. See, e.g., U.S. Pat. No. 5,185,440, and other references cited herein.

The studies of these viruses have led to the development of techniques for vaccination against the alphavirus diseases and against other diseases through the use of alphavirus vectors for the introduction of foreign DNA encoding antigens of interest. See U.S. Pat. No. 5,185,440 to Davis et al., and PCT Publication WO 92/10578. The introduction of foreign expressible DNA into eukaryotic cells has become a topic of increasing interest. It is well known that live, attenuated viral vaccines are among the most successful means of controlling viral disease. However, for some viral (or other) pathogens, immunization with a live virus strain may be either impractical or unsafe. One alternative strategy is the insertion of sequences encoding immunizing antigens of such agents into a live, replicating strain of another virus. One such system utilizing a live VEE vector is described in U.S. Pat. No. 5,505,947 to Johnston et al. Another such system is described by Hahn et al., 1992, *Proc. Natl. Acad. Sci. USA* 89:2679-2683, wherein Sindbis virus constructs express a truncated form of the influenza hemagglutinin protein. Another approach is the use of infective, propagation-defective alphavirus particles, as described in U.S. Pat. No. 6,190,666 to Garoff et al., U.S. Pat. Nos. 5,792,462 and 6,156,558 to Johnston et al., U.S. Published Application No. 2002/0015945 A1 (Polo et al.), U.S. Published Application No. 2001/0016199 (Johnston et al.), Frolov et al., 1996, *Proc. Natl. Acad. Sci. USA* 93:11371-11377 and Pushko et al. (1997) *Virology* 239:389-401. Alphaviruses have also been shown to be relatively easy to genetically manipulate, as reflected by a number of applications using alphaviruses as genomic expression libraries, e.g., see U.S. Pat. No. 6,197,502. The use of Semliki Forest Virus (SFV) vectors expressing a library of antigens has also been explored in animal models where SFV particles expressing a library of tumor antigens were used to infect dendritic cells in vitro and the dendritic cells were used to immunize mice showing some protection in a glioma model (Yamanaka et al., 2001, *J. Neurosurg.* 94:474-81).

There is a longfelt need in the art for nucleic acid sequences encoding foreign antigens which can be used to immunize a person or an animal against neoplastic conditions or against parasite or pathogen infection, especially where there is no attenuated strain or where the neoplasia, parasite or pathogen is not well characterized at the molecular level, or where it is recognized that protective immunization requires the expression of multiple antigens.

SUMMARY OF THE INVENTION

It is an object of the present invention to provide a virus replicon particle preparation derived from a neoplastic cell, pathogen or a parasite and immunogenic compositions comprising same. The preparation contains a multiplicity of expressible coding sequences derived from the neoplastic cell, pathogen or parasite, and expression of the coding sequences in a human or animal patient to whom the preparation is administered results in the generation of an immune response to the multiplicity of antigenic determinants encoded by and expressed from the alphavirus replicon nucleic acid. The immunogenic composition comprises the alphavirus replicon particle preparation of interest and a pharmaceutically acceptable carrier, and advantageously further comprises an immunological adjuvant and/or a cytokine to improve or stimulate the immune response. The alphavirus replicon can be any alphavirus replicon RNA vector derived from VEE, Sindbis virus, South African Arbovirus No. 86, Semliki Forest virus, among others. In preferred embodiments, the alphavirus vector contains one or more attenuating mutations. Suitable mutations, as well as methods to identify them, have been described (see, for example, U.S. Pat. Nos. 5,505,947; 5,639,650; 5,811,407).

Routes of administration can include subcutaneous (s.c.), intraperitoneal (i.p.), intramuscular (i.m.), intradermal (i.d.), intravenous (i.v.), intratumoral, intracerebral (i.c.), direct lymph node inoculation (i.n.), and mucosal routes such as nasal, bronchial, intrarectal, intravaginal and oral routes. Intramuscular administration is advantageous.

Dosages in humans and animals can range from about $1 \times 10^4$ to about $1 \times 10^{10}$, advantageously at a dose of about $1 \times 10^6$ to about $1 \times 10^8$ per dose. For the vaccine-type immunogenic approaches, the present inventors contemplate weekly, biweekly or monthly doses for a period of about 1 to about 12 months, or longer. This can be followed by booster vaccinations, on an as needed basis, e.g. annually.

Especially in the case where the alphavirus replicon preparation is derived from tumor cells from a specific patient, a patient specific vaccine preparation is made and administered back to the same individual; i.e. the autologous vaccine approach. Also within the scope of the present invention is an allogeneic approach, in which the viral replicon population derived from one patient's tumor cells is administered to another patient suffering from, believed to be suffering from or at high risk for the same neoplastic condition. An example of a high risk patient is an individual with a genetic predisposition or proven hereditary increased risk for cancer. For example, breast cancer is associated with high familial risk in female family members of patients suffering from breast cancer. Similarly, one might vaccinate an HIV positive individual and at the same time, prophylactically vaccinate their non-infected partner with the same vaccine preparation to try to prevent the uninfected individual from becoming infected.

The present invention further encompasses following the immune responses elicited by administration of a virus replicon preparation or an immunogenic composition comprising the same in a patient to identify those tumor antigens to which the patient has responded. These responses can be humoral and/or cellular. This approach allows the identification of novel antigens and enables the use of a more defined population of antigens with which to immunize the patient. This can be accomplished by administering boosts with more limited ARP preparations or by carrying out subsequent immunizations of other patients or individuals (in a prophylactic regimen) with the more defined set of antigen-encoding ARP-containing immunogenic preparations.

The present invention also relates to the treatment and/or prevention of infectious diseases and parasite infestations. Using HIV as an example, a successful multi-antigenic HIV ARP vaccine derived from a patient-specific HIV gene or genes directly from an individual's own viral population can be applied to persons infected with a similar genetic strain of virus or persons exposed, likely to be exposed or potentially exposed to a similar strain. Particularly, immunogenic or novel immunogens from the pathogen or parasite of interest can be identified using the ARPs as a tool to identify new immunogenic proteins. Similarly, multiple strains of a disease causing virus (such as the recognized clades of HIV) or parasite can be combined into the ARP preparation of this invention to provide robust, immunogenic compositions which are not strain-specific. For example, several different clades of HIV have been recognized, and they can be combined to provide a multi-clade HIV vaccine.

In the case of cancer patients, the administration of ARPs carrying expressible cancer cell antigenic determinants' coding sequences is advantageously accompanied by chemotherapeutic treatments, especially where chemotherapeutic treatments do not ablate the ability of the immune system to respond to antigens expressed after the administration of immunogenic compositions comprising the ARPs of the present invention.

The ARP preparations of the present invention, expressing antigens characteristic of a particular type of tumor or cancer, a virus, a bacterial, fungal or protozoan pathogen or a parasite can be administered in prophylactic or therapeutic treatment regimens, and administration of the ARPs can be carried out in combination with other immunogenic preparations for priming and/or boosting, for example, using an ARP vaccine prime and dendritic cell vaccine boost, or an ARP prime and an adenoviral vector boost. All possible combinations of DNA, RNA, adenoviruses, picornaviruses, adeno-associated viruses, poxviruses, retroviruses, aphthoviruses, nodaviruses, flaviviruses, dendritic cell, peptides, heat shock proteins, minigenes, whole tumor cells and tumor cell lysate vaccines can be used in conjunction with the ARPs expressing a multiplicity of antigens of interest of the present invention. Adjuvants such as cytokines or chemokines, or ARPs which direct the expression of chemokines or cytokines, can be utilized in the preparations of the present invention. The addition of heterologous prime/boosts in combination with the ARP expressing a multiplicity of genes would likely be with vector replicons or sets of vector replicons expressing single or a relatively small number of tumor antigens. This functions so as to focus the immune system on specific antigens following or prior to a broader immune response elicited by the ARP(s). Similar such heterologous delivery systems may be used in combination with the present alphavirus replicon expression libraries to enhance and/or maintain addition memory and longterm immune functions.

A further object of the present invention is the administration of the ARP-containing immunogenic compositions of the present invention to a human not only to treat cancer or other pathological states in a therapeutic setting when the patient is positive for tumor, pathogen or parasite, but also once treatment is successful and the patient is in remission. Such ongoing periodic (booster) immunization can facilitate maintenance of a tumor-free, disease-free or parasite-free state and prevent regression or recurrence of the tumor or disease, respectively.

A further object of the present invention is the administration of the ARP-containing immunogenic compositions of the present invention to an animal (e.g. horse, pig, cow, goat, primate, rabbit, mouse, hamster, avian) to generate immune responses, such as antibodies. Sera or cells collected from such animals are useful in providing polyclonal sera or cells for the production of hybridomas that generate monoclonal sera, such antibody preparations being useful in research, diagnostic and therapeutic applications.

A further object of the invention is a method for preparing alphaviral replicon particles (ARPs) which collectively encode a multiplicity of antigens from a tumor, a tumor cell, pathogen or parasite. The method includes the steps of preparing DNA or cDNA from the tumor, a tumor cell, pathogen or parasite of interest and cloning into the virus/alphavirus replicon nucleic acid to produce a modified virus/alphavirus replicon nucleic acid, introducing the modified viral/alphaviral replicon nucleic acid into a permissive cell, said modified viral/alphaviral replicon nucleic acid containing at least a virus packaging signal to produce a modified permissive cell, culturing the modified permissive cell under conditions allowing expression of at least one helper function and allowing replication of said modified viral/alphaviral nucleic acid and packaging to form ARPs, and desirably contacting the cultured permissive cells with a Release Medium to release cell- and debris-bound ARPs. The modified viral/alphaviral replicon nucleic acid can be introduced into permissive cells which already contain and express coding sequences required for packaging, or one or more "helper" DNA or RNA molecules carrying packaging genes can be introduced together with the modified viral/alphaviral replicon nucleic acid. Optionally, the Release Medium step can be preceded by a wash step which does not result in the release of the ARPs from the cells. Advantageously the wash step includes DNase treatment, or DNA can be digested in an ARP preparation with DNase. DNase, for example, from *Serratia marcescens*, can be used at a concentration from 10-1000 units per mL, with incubation from 10 to 60 minutes at 370. The Release Medium is an aqueous medium which desirably is from about pH 6 to 9, desirably from about 6.5 to about 8.5, and contains from about 0.2 to about 5 M of a salt including but not limited to ammonium acetate, ammonium chloride, sodium chloride, magnesium chloride, calcium chloride, potassium chloride, ammonium sulfate and sodium bicarbonate. It is advantageous that when modified alphaviral replicon nucleic acids are introduced into the permissive cells by electroporation, the cells are present in a density of from about $10^7$ to about $5 \times 10^8$ per mL of electroporation mixture.

Advantageously, the cells in which the ARPs are to be produced are synchronized in the G2/M phase of the cell cycle prior to electroporation with the alphavirus replicon vector and helper nucleic acid(s). Without wishing to be bound by any particular theory, it is believed that greater electroporation efficiency and transfer of nucleic acid to the nucleus (in those embodiments of the invention that involve nuclear activity) of the electroporated cell is achieved in such G2/M phase cells.

BRIEF DESCRIPTION OF THE DRAWING

FIG. 1 is a bar graph depicting antigen-specific immune responses in animals vaccinated with multi-antigenic ARP. Antigen-specific immune responses (in the form of humoral immunity) as measured by either ELISA and presented as reciprocal geometric mean titer, or Western blot or IFA and presented as the lowest dilution at which antigen specific signal was detectable. Antigen specific immune responses in the form of cellular immunity as measured by ELISPOT detection of IFN-γ secreting cells and presented as antigen specific IFN-γ secreting lymphocytes per $10^6$ lymphocytes. Animals which received the multi-antigenic ARP preparation either by a subcutaneous (s.c.) or an intraperitoneal (i.p.) route of inoculation mounted immune responses to all antigens in the preparation. As a positive control, one group received HIV-Gag ARP and mounted immune responses only specific for Gag. Negative control animals had no detectable response to any antigen.

DETAILED DESCRIPTION OF THE INVENTION

In the context of the present application, nm means nanometer, mL means milliliter, μL means microliter, pfu/mL means plaque forming units/milliliter, iu means infectious units, VEE means Venezuelan Equine Encephalitis virus, EMC means Encephalocomyocarditis virus, BHK means baby hamster kidney cells, HA means hemagglutinin gene, CAT means chloramphenicol acetyl transferase, β-gal means β-galactosidase, GFP means green fluorescent protein gene, N means nucleocapsid, FACS means fluorescence activated cell sorter, ELISA means enzyme-linked immunosorbent assay, and IRES means internal ribosome entry site. The expression "E2 amino acid (e.g., Lys, Thr, etc.) number" indicates designated amino acid at the designated residue of the E2 gene, and is also used to refer to amino acids at specific residues in the E1 gene.

The term "alphavirus" has its conventional meaning in the art, and includes the various species of alphaviruses such as Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, South African Arbovirus No. 86, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J Virus, Fort Morgan Virus, Ndumu Virus, and Buggy Creek Virus. The preferred alphavirus RNA transcripts for use in the present invention include VEE Virus, Sindbis Virus, South African Arbovirus No. 86, and Semliki Forest Virus RNA transcripts.

Alphavirus-permissive cells employed in the methods of the present invention are cells which, upon transfection with an alphaviral RNA transcript, are capable of producing viral particles. Alphaviruses have a broad host range. Examples of suitable host cells include, but are not limited to Vero, baby hamster kidney (BHK), DF1, CHO, 293, 293T, chicken embryo fibroblast and insect cells such as SF21, *Spodoptera frugiperda*; C6/36, *Aedes albopictus*; TRA-171, *Toxorhynchites amboinensis*; RML-12, *Aedes aegypti*; AP-61, *Aedes pseudoscutellaris*; and MOS-55, *Anopheles gambiae* cells.

The phrases "structural protein" or "alphavirus structural protein" as used herein refer to the virally encoded proteins which are required for encapsidation of the RNA replicon into a replicon particle, and include the capsid protein, E1 glycoprotein, and E2 glycoprotein. As described herein, the structural proteins of the alphavirus are distributed among one or more helper nucleic acids. For example, a first helper RNA and a second helper RNA can be used, or a single DNA helper encoding all alphavirus structural proteins, can be used. In addition one or more structural proteins may be located on the same RNA molecule as the replicon RNA, provided that at least one structural protein is deleted from the replicon RNA such that the replicon and resulting alphavirus particle are propagation-defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "replication defective" as used herein is synonymous with "propagation-defective", and means that the particles produced in a given host cell cannot produce progeny particles in the other host cell, due to the absence of the helper function, i.e. the alphavirus structural proteins required for packaging the replicon nucleic acid. However, the replicon nucleic acid is capable of replicating itself and being expressed within the host cell into which it has been introduced.

The helper cell, also referred to as a packaging cell, used to produce the infectious, propagation defective alphavirus particles, must express or be capable of expressing alphavirus structural proteins sufficient to package the replicon nucleic acid. The structural proteins can be produced from a set of RNAs, typically two, that are introduced into the helper cell concomitantly with or prior to introduction of the replicon vector. The first helper RNA includes RNA encoding at least one alphavirus structural protein but does not encode all alphavirus structural proteins. The first helper RNA may comprise RNA encoding the alphavirus E1 glycoprotein, but not encoding the alphavirus capsid protein and the alphavirus E2 glycoprotein. Alternatively, the first helper RNA may comprise RNA encoding the alphavirus E2 glycoprotein, but not encoding the alphavirus capsid protein and the alphavirus E1 glycoprotein. In a further embodiment, the first helper RNA may comprise RNA encoding the alphavirus E1 glycoprotein and the alphavirus E2 glycoprotein, but not the alphavirus capsid protein. In a fourth embodiment, the first helper RNA may comprise RNA encoding the alphavirus capsid, but none of the alphavirus glycoproteins. In a fifth embodiment, the first helper RNA may comprise RNA encoding the capsid and one of the glycoproteins, i.e. either E1 or E2, but not both.

In combination with any one of these first helper RNAs, the second helper RNA encodes at least one alphavirus structural protein not encoded by the first helper RNA. For example, where the first helper RNA encodes only the alphavirus E1 glycoprotein, the second helper RNA may encode one or both of the alphavirus capsid protein and the alphavirus E2 glycoprotein. Where the first helper RNA encodes only the alphavirus capsid protein, the second helper RNA may include RNA encoding one or both of the alphavirus glycoproteins. Where the first helper RNA encodes only the alphavirus E2 glycoprotein, the second helper RNA may encode one or both of the alphavirus capsid protein and the alphavirus E1 glycoprotein. Where the first helper RNA encodes both the capsid and alphavirus E1 glycoprotein, the second helper RNA may include RNA encoding one or both of the alphavirus capsid protein and the alphavirus E2 glycoprotein.

In all of the helper nucleic acids, it is understood that these molecules further comprise sequences necessary for expression (encompassing translation and where appropriate, transcription or replication signals) of the encoded structural protein sequences in the helper cells. Such sequences can include, for example, promoters (either viral, prokaryotic or eukaryotic, inducible or constitutive) and 5' and 3' viral replicase recognition sequences. In the case of the helper nucleic acids expressing one or more glycoproteins, it is understood from the art that these sequences are advantageously expressed with a leader or signal sequence at the N-terminus of the structural protein coding region in the nucleic acid constructs. The leader or signal sequence can be derived from the alphavirus, for example E3 or 6k, or it can be a heterologous sequence such as a tissue plasminogen activator signal peptide or a synthetic sequence. Thus, as an example, a first helper nucleic acid may be an RNA molecule encoding capsid-E3-E1, and the second helper nucleic acid may be an RNA molecule encoding capsid-E3-E2. Alternatively, the first helper RNA can encode capsid alone, and the second helper RNA can encode E3-E2-6k-E1. Additionally, the packaging signal or "encapsidation sequence" that is present in the viral genome is not present in all of the helper nucleic acids. Preferably, the packaging signal is deleted from all of the helper nucleic acids.

These RNA helpers can be introduced into the cells in a number of ways. They can be expressed from one or more expression cassettes that have been stably transformed into the cells, thereby establishing packaging cell lines (see, for example, U.S. Pat. No. 6,242,259). Alternatively, the RNAs can be introduced as RNA or DNA molecules that can be expressed in the helper cell without integrating into the cell's genome. Methods of introduction include electroporation, viral vectors (e.g. SV40, adenovirus, nodavirus, astrovirus), and lipid-mediated transfection.

An alternative to multiple helper RNAs is the use of a single nucleic acid molecule which encodes all the functions necessary for replicating the viral replicon RNA and synthesizing the polypeptides necessary for packaging the alphaviral replicon RNA into infective alphavirus replicon particles. This can be accomplished with an RNA molecule determining the necessary functions or a DNA molecule determining the necessary functions. The single DNA helper nucleic acid can be introduced into the packaging cell by any means known to the art, including but not limited to electroporation, lipid-mediated transfection, viral vectored (e.g. adenovirus or SV-40), and calcium phosphate-mediated transfection. Preferably, the DNA is introduced via the electroporation-based methods of this invention, with voltage and capacitance optimized for the cells and nucleic acid(s) being introduced. The DNA is typically electroporated into cells with a decrease in voltage and an increase in capacitance, as compared to that required for the uptake of RNA. In all electroporations, the value for the voltage and capacitance must be set so as to avoid destroying the ability of the packaging cells to produce infective alphavirus particles. The DNA was highly purified to remove toxic contaminants and concentrated to about 5 mg/mL prior to electroporation. Generally, it is preferable to concentrate the DNA to between 1-8 mg/mL, preferably between 5 and 8 mg/mL. The DNA helper is present in the electroporation mixture at from about 20-500, desirably from about 50 to about 300, for example about 150 µg per 0.8 mL electroporation mixture, desirably containing from about $5 \times 10^7$ to about $2 \times 10^8$ cells, for example, about $1.2 \times 10^8$ cells.

Alternatively, the helper function, in this format and under an inducible promoter, can be incorporated into the packaging cell genome prior to the introduction/expression of the viral RNA vector replicon nucleic acid, and then induced with the appropriate stimulus just prior to, concomitant with, or after the introduction of the RNA vector replicon.

Advantageously, the nucleic acid encoding the alphavirus structural proteins, i.e., the capsid, E1 glycoprotein and E2 glycoprotein, contains at least one attenuating mutation. The phrases "attenuating mutation" and "attenuating amino acid," as used herein, mean a nucleotide mutation or an amino acid coded for in view of such a mutation which result in a decreased probability of causing disease in its host (i.e., a loss of virulence), in accordance with standard terminology in the art, See, e.g., B. Davis, et al. *Microbiology* 132 (3d ed. 1980), whether the mutation be a substitution mutation, or an in-frame deletion or addition mutation. The phrase "attenuating mutation" excludes mutations which would be lethal to the virus unless such a mutation is used in combination with a "restoring" mutation which renders the virus viable, albeit attenuated. In specific embodiments, the helper nucleic acid (s) include at least one attenuating mutation.

Methods for identifying suitable attenuating mutations in the alphavirus genome are known in the art. Olmsted et al.

(1984; Science 225:424) describes a method of identifying attenuating mutations in Sindbis virus by selecting for rapid growth in cell culture. Johnston and Smith (1988; Virology 162:437) describe the identification of attenuating mutations in VEE by applying direct selective pressure for accelerated penetration of BHK cells. Attenuating mutations in alphaviruses have been described in the art, e.g. White et al. 2001 *J. Virology* 75:3706; Kinney et al. 1989 *Virology* 70:19; Heise et al. 2000 *J. Virology* 74:4207; Bernard et al 2000 *Virology* 276:93; Smith et al 2001 *J. Virology* 75:11196; Heidner & Johnston 1994 *J. Virology* 68:8064; Klimstra et al. 1999 *J. Virology* 73:10387; Glasgow et al. 1991 *Virology* 185:741; Polo and Johnston 1990 *J. Virology* 64:4438; and Smerdou and Liljestrom 1999 *J. Virology* 73:1092.

In certain embodiments, the replicon RNA comprises at least one attenuating mutation. In other specific embodiments, the helper nucleic acid molecule(s) include at least one attenuating mutation. In the embodiment comprising two helper nucleic acid molecules, at least one molecule includes at least one attenuating mutation, or both can encode at least one attenuating mutation. Alternatively, the helper nucleic acid, or at least one of the first or second helper nucleic acids includes at least two, or multiple, attenuating mutations. Appropriate attenuating mutations depend upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threonine as E1 amino acid 253. Additional attenuating mutations include deletions or substitution mutations in the cleavage domain between E3 and E2 such that the E3/E2 polyprotein is not cleaved; this mutation in combination with the mutation at E1-253 is a preferred attenuated strain for use in this invention. Similarly, mutations present in existing live vaccine strains, e.g. strain TC83 (see Kinney et al., 1989, Virology 170: 19-30, particularly the mutation at nucleotide 3), are also advantageously employed in the particles purified by the methods of this invention. An example of an attenuating mutation in the non-coding region of the replicon nucleic acid is the substitution of A or C at nucleotide 3 in VEE.

Suitable helper and viral replicon RNAs are disclosed in U.S. Pat. No. 6,156,558, which is incorporated herein by reference.

Where the alphavirus is the South African Arbovirus No. 86 (S.A. AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid position 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art.

Attenuating mutations may be introduced into the nucleic acid by performing site-directed mutagenesis, in accordance with known procedures. See, Kunkel, *Proc. Natl. Acad. Sci. USA* 82:488 (1985), the disclosure of which is incorporated herein by reference in its entirety. Alternatively, mutations may be introduced into the nucleic acid by replacement of homologous restriction fragments, in accordance with known procedures, or by mutagenic polymerase chain reaction methods.

Once the helper nucleic acid(s) and replicon RNAs for use in producing ARPs are generated, they are introduced into suitable host cells, desirably by electroporation. The present inventors discovered that the electroporation carried out at relatively high cell density allows efficient uptake of helper nucleic acid and virus replicon RNAs. The helper and replicon nucleic acids should be purified for use in electroporation or other protocols for introducing the nucleic acids into cells for ARP production, but the helper RNAs need not be capped.

The step of producing the infectious viral particles in the cells may also be carried out using conventional techniques. See e.g., U.S. Pat. No. 5,185,440 to Davis et al., PCT Publication No. WO 92/10578 to Bioption A B, and the U.S. Pat. No. 4,650,764 to Temin et al. (although Temin et al., relates to retroviruses rather than alphaviruses). The infectious viral particles may be produced by standard cell culture growth techniques improved by procedures described herein and/or by conventional particle harvesting techniques or the salt wash procedure described hereinbelow. The salt wash appears to improve ARP recovery, especially when there are particular surface charges on the ARP surface. In the case of VEE, amino acid residues at E2=309 and E2-120 provide good sites for introducing a positive charge.

The viral replicon RNAs encode multiple heterologous coding sequences which are operably linked to promoters and other sequences required for transcriptional and translational expression of the coding sequence in the host cell where the ARPS are to be introduced and expressed.

Any amino acids which occur in the amino acid sequences referred to in the specification have their usual three- and one-letter abbreviations routinely used in the art: A, Ala, Alanine; C, Cys, Cysteine; D, Asp, Aspartic Acid; E, Glu, Glutamic Acid; F. Phe, Phenylalanine; G, Gly, Glycine; H, His, Histidine; I, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

As used herein "expression" directed by a particular sequence is the transcription of an associated downstream sequence. If appropriate and desired for the associated sequence, there the term expression also encompasses translation (protein synthesis) of the transcribed RNA. Alternatively, different sequences can be used to direct transcription and translation.

Genomic DNA (where genes are not interrupted by introns and/or where this is not a significant proportion of the genome devoted to highly repeated or non-expressed sequences) or cDNA is cloned into a suitably prepared virus vector nucleic acid preparation to produce a recombinant vector nucleic acid preparation. The recombinant vector nucleic acid preparation is then introduced into cells which allow packaging of the recombinant vector nucleic acids into infective particles. The recombinant vector nucleic acid preparation can be electroporated into cells for packaging together with helper nucleic acids, RNA or DNA, in a relatively high cell density electroporation, e.g. about $10^7$ to about $10^9$ cells/per mL electroporation mixture. The cells are then cultured in growth medium to allow packaging of the recombinant vector nucleic acids into viral replicon particles.

After the ARPs have been collected from the cells by salt wash, and desirably collected from the cell free supernatant, the ARPs are partially purified by ion exchange chromatography.

The methods of the present invention are advantageously applied to viral replicon nucleic acids derived from an alphavirus, preferably from an attenuated alphavirus. A particularly preferred alphavirus is Venezuelan equine encephalitis virus (VEE). A specifically exemplified attenuated VEE is strain 3014, which virus or ARPs derived therefrom can be purified using heparin affinity chromatography. VEE strain 3042 is another attenuated virus suitable for use in ARP methods, but the coat of this virus or ARPs derived therefrom cannot be purified using heparin affinity chromatography. The viruses, or ARPs derived therefrom, that carry mutations conferring glycosaminoglycan-binding ability are particularly well suited for purification using the salt wash step, and they can also be further purified using heparin affinity chromatography.

Cancers (neoplastic conditions) from which cells can be obtained for use in the methods of the present invention include carcinomas, sarcomas, leukemias, and cancers derived from cells of the nervous system. These include, but are not limited to: brain tumors, such as astrocytoma, oligodendroglioma, ependymoma, medulloblastomas, and Primitive Neural Ectodermal Tumor (PNET); pancreatic tumors, such as pancreatic ductal adenocarcinomas; lung tumors, such as small and large cell adenocarcinomas, squamous cell carcinoma and bronchoalveolarcarcinoma; colon tumors, such as epithelial adenocarcinoma and liver metastases of these tumors; liver tumors, such as hepatoma and cholangiocarcinoma; breast tumors, such as ductal and lobular adenocarcinoma; gynecologic tumors, such as squamous and adenocarcinoma of the uterine cervix, and uterine and ovarian epithelial adenocarcinoma; prostate tumors, such as prostatic adenocarcinoma; bladder tumors, such as transitional, squamous cell carcinoma; tumors of the reticuloendothelial system (RES), such as B and T cell lymphoma (nodular and diffuse), plasmacytoma and acute and chronic leukemia; skin tumors, such as melanoma; and soft tissue tumors, such as soft tissue sarcoma and leiomyosarcoma.

The terms "neoplastic cell", "tumor cell", or "cancer cell", used either in the singular or plural form, refer to cells that have undergone a malignant transformation that makes them harmful to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

Pathogens to which multiple antigen immunological responses are advantageous include viral, bacterial, fungal and protozoan pathogens. Viruses to which immunity is desirable include, but are not limited to, hemorrhagic fever viruses (such as Ebola virus), immune deficiency viruses (such as feline or human immunodeficiency viruses), herpesviruses, coronaviruses, adenoviruses, poxviruses, retroviruses, aphthoviruses, nodaviruses, picornaviruses, orthomyxoviruses, paramyxoviruses, rubella, togaviruses, flaviviruses, bunyaviruses, reoviruses, oncogenic viruses such as retroviruses, pathogenic alphaviruses (such as Semliki forest virus or Sindbis virus), rhinoviruses, hepatitis viruses (Group B, C, etc), influenza viruses, among others. Bacterial pathogens to which immune responses are helpful include, without limitation, staphylococci, streptococci, pneumococci, salmonellae, escherichiae, yersiniae, enterococci, clostridia, corynebacteria, *hemophilus*, neisseriae, *bacteroides, francisella*, pasteurellae, brucellae, mycobacteriae, bordetella, spirochetes, actinomycetes, chlamydiae, mycoplasmas, rickettsiae, and others. Pathogenic fungi of interest include but are not limited to *Candida*, cryptococci, *blastomyces, histoplasma, coccidioides*, phycomycetes, trichodermas, aspergilli, *pneumocystis*, and others. Protozoans to which immunity is useful include, without limitation, toxoplasma, plasmodia, schistosomes, amoebae, *giardia, babesia, leishmania*, and others. Other parasites include the roundworms, hookworms and tapeworms, filiaria and others.

One of the strengths of the present alphavirus replicon vector technology is the ability to express more than one foreign gene. Until now, alphaviral replicon vaccines have been limited to the expression of single or a handful of heterologous genes. This ability to express more than one heterologous gene has been achieved through the addition of multiple promoter units to drive each individual gene's expression. The number of heterologous genes a replicon vector can carry is ultimately constrained by the capsid structure which is limited in the amount of nucleic acid it can accommodate. An alternate strategy to single replicons expressing two or three antigens is to administer a cocktail of individual alphavirus replicon particles, each encoding and expressing different antigens to elicit an immune response against multiple antigens and/or infectious agents as described herein. To date, these approaches have been limited to the expression of only a few antigens at the same time (~3), either in the multi-promoter or the cocktail replicon setting.

However, the recent improvements in process technology as described herein for the generation of alphavirus replicon particles have opened the door to new opportunities in vaccination against multiple antigens in the same vaccine preparation. The process improvements are based on a high cell density electroporation method (cell concentration of $5\times10^7$ to $1.5\times10^8$ cells/mL of electroporation mixture) and salt wash techniques. Other improvements include the use of uncapped (or capped) RNA molecules or DNA molecules in the electroporation mixture. Yields from these improvements have been increased by 2 to 3 orders of magnitude (up to $10^{11}$ i.u. can be produced from a single cuvette electroporation). These significant increases in efficiency of replicon production over the existing art mean a number of vaccine approaches that were previously not feasible from a scale standpoint are now enabled. The yield which can be achieved using the present methods, disclosed herein and in the referenced provisional applications, in theory, allows the production of ARPs which express the full range of antigens expressed by the tumor, tumor cell, pathogen or parasite from which the nucleic acid inserted into the viral replicon nucleic acid was prepared.

One such approach is a "patient-specific vaccine" where a single vaccine preparation is prepared on a patient-by-patient basis for prophylactic or therapeutic treatment of infectious diseases or neoplastic condition, e.g., cancer. Because a single tumor cell is estimated to express up to 5,000 genes, any attempt to generate an alphaviral replicon tumor library vaccine expressing this large a number of genes using traditional approaches would have been significantly limited in the number of replicons expressing each gene. In addition, the particles would require purification to be suitable for formulation and administration in a clinical setting, and purification often results in a significant additional loss of titer. Using the improved ARP production techniques, we can now generate a population of replicons where most, if not all, genes from the tumor cell are likely represented, on average, at least once in a population of $1 \times 10^5$ particles. In addition to the high yields from this approach, the process may provide a purer formulation on a per infectious unit basis. This means sequential purification steps may not be required, thus preventing subsequent process losses. In addition, the increased purity may lower the risk of eliciting anti-vector and anti-contaminant immune responses in the host. Normally, such a response could potentially prevent or compromise the efficacy of booster vaccinations. For approaches such as therapeutic tumor treatment, the ability to deliver high titers of vaccine in a pure formulation at frequent intervals is a key desirable characteristic of a vaccine. The present invention enables a new multi-antigenic library approach to be taken using alphaviral replicon vectors. These libraries can encode either multiple antigens, or entire gene repertoires from pathogenic organisms, parasites or tumor cells.

While prior art methods used to produce nucleic acids for introduction into cells for ARP production are expensive and labor intensive, the present disclosure describes modifying various parameters to achieve improved ARP yield while simplifying the process and decreasing the cost per ARP by orders of magnitude. The improved alphavirus particle yield has enabled cloning nucleic acids derived from a tumor cell, pathogen or parasite into an alphavirus replicon nucleic acid and packaging with sufficient efficiency such that a representative set of tumor cell, pathogen or parasite antigens are produced by the ARP "expression library". The yield of ARPs is also sufficiently high such that a human or animal patient can be inoculated with an aliquot of such an ARP preparation, with the preparation optionally further containing an immunological adjuvant, so that immune responses are generated to a multiplicity of antigenic determinants encoded within the ARP library and preparation administered to the patient.

Table 1 shows titration of multi-antigenic ARP produced from a pool of cDNAs. Alphavirus replicon constructs expressing 10 different heterologous genes (chloramphenicol acetyltransferase (CAT), beta-galactosidase (β-gal), Rat/Neu oncogene, luciferase, HIV Gag, cancer antigen A, and four malarial antigens: PkMSP1-42, PyHep17, PfAMA1 and PkCSP) were linearized with NotI restriction endonuclease, pooled and RNA transcripts generated using T7 RNA polymerase. The pool of RNA molecules were co-electroporated into VERO cells with alphaviral capsid and glycoprotein helper RNAs to produce a population of ARP consisting of individual ARP expressing all 10 different antigens as determined by ARP titration using immunofluorescence assays specific for each gene product.

Table 2 shows titration of multi-antigenic ARP produced from a pool of RNAs. Alphavirus replicon constructs expressing 7 different heterologous genes (CMV IE1, CMV gB, Influenza HA, HIV Pol, HIV Gag, Rat/neu, CAT) were individually linearized with NotI restriction endonuclease. RNA transcripts for each replicon were generated using T7 RNA polymerase. The seven different RNA transcription products were mixed at equivalent concentrations and were co-electroporated into VERO cells with alphaviral capsid and glycoprotein helper RNAs. A population of ARP was produced which expressed all 7 different antigens as determined by ARP titration using immunofluorescence assays specific for each gene product.

Table 3 provides a summary of antigen-specific immune responses in animals vaccinated with multi-antigenic ARP (as shown in FIG. 1). Antigen-specific immune responses in the form of humoral immunity are measured by either ELISA and presented as reciprocal geometric mean titer, or Western blot or IFA and presented as the lowest dilution at which antigen-specific signal was detectable. Antigen specific immune responses in the form of cellular immunity are measured by ELISPOT detection of IFN-γ secreting cells and presented as antigen specific IFN-γ secreting lymphocytes per $10^6$ lymphocytes. Animals which received the multi-antigenic ARP preparation either by a s.c. or an i.p. route of inoculation mounted immune responses to all antigens in the preparation. As a positive control, one group received HIV-Gag ARP and mounted immune responses only specific for Gag. Negative control animals had no detectable response to any antigen. Many samples were not titrated to endpoint, and are presented as titers equal to or greater than the given value. Notably, the immune response elicited to the HIV Gag gene protein as part of the multiantigenic preparations was equivalent on a humoral and cellular basis as compared to the HIV Gag protein delivered as a single (homogeneous) standard preparation. This demonstrates coding sequences expressed as a component of a larger expression library can still be effectively immunogenic employing the compositions and methods of this invention.

The immunological ARP preparations which comprise expressible nucleotide sequences encoding a multiplicity of tumor cell, pathogen or parasite antigenic determinants can be administered as a part of a prophylactic regimen, i.e., to lower the probability that the human or animal to which the preparation is administered suffers from the neoplastic condition, pathogen infection or parasite infection, or as a therapeutic regimen, to lessen the severity of any conditions associated with an existing neoplastic condition, pathogen infection or parasite infection or such that the neoplastic condition, pathogen infection or parasite infection is prevented due to an immune response generated in the human or animal to which the preparation has been administered.

While the generation of an immune response includes at least some level of protective immunity directed to the tumor cell (or neoplastic condition), pathogen or parasite, the clinical outcome in the patient suffering from such a neoplastic condition or infection with a parasite or a pathogen can be improved by also treating the patient with a suitable chemotherapeutic agent, as known to the art. Where the pathogen is viral, an anti-viral compound such as acyclovir can be administered concomitantly with ARP vaccination, for example, in patients with herpesvirus infection, or HAART (highly active anti-retroviral therapy) in individuals infected with HIV. Where the pathogen is a bacterial pathogen, an antibiotic to which that bacterium is susceptible is desirably administered and where the pathogen is a fungus a suitable antifungal antibiotic is desirably administered. Similarly, chemical agents for the control and/or eradication of parasitic infections are known and are advantageously administered to the human or animal patients using dosages and schedules well known to the art. Where the patient is suffering from a neoplastic condition, for example, a cancer, the administration of the immunogenic composition comprising ARPs capable of expressing a multiplicity of cancer-associated antigens in the patient to which it has been administered is desirably accompanied by administration of antineoplastic agent(s), including, but not limited to, such chemotherapeutic agents as daunorubicin, taxol thioureas, cancer-specific antibodies linked with therapeutic radionuclides, with the proviso that the agent(s) do not ablate the ability of the patient to generate an immune response to the administered ARPs and the antigens whose expression they direct in the patient.

Pharmaceutical formulations, such as vaccines or other immunogenic compositions, of the present invention comprise an immunogenic amount of the infectious, propagation-defective alphavirus replicon particles in combination with a pharmaceutically acceptable carrier. An "immunogenic amount" is an amount of the infectious alphavirus particles which is sufficient to evoke an immune response in the subject to which the pharmaceutical formulation is administered. An amount of from about $10^1$ to about $10^{10}$ infectious units per dose, preferably $10^5$ to $10^8$, is believed suitable, depending upon the age and species of the subject being treated. Exemplary pharmaceutically acceptable carries include, but are not limited to, sterile pyrogen-free water and sterile pyrogen-free physiological saline solution. Subjects which may be administered immunogenic amounts of the infectious, propagation defective alphavirus particles of the present invention include but are not limited to human and animal (e.g., dog, cat, horse, pig, cow, goat, rabbit, donkey, mouse, hamster, monkey) subjects. Immunologically active compounds such as cytokines and/or BCG can also be added to increase the immune response to the administered viral replicon particle preparation. Administration may be by any suitable means, such as intratumoral, intraperitoneal, intramuscular, intradermal, intranasal, intravaginal, intrarectal, subcutaneous or intravenous administration.

Immunogenic compositions comprising the ARPs (which direct the expression of the antigens of interest when the compositions are administered to a human or animal) produced using the methods of the present invention may be formulated by any of the means known in the art. Such compositions, especially vaccines, are typically prepared as injectables, either as liquid solutions or suspensions. Solid forms, for example, lyophilized preparations, suitable for solution in, or suspension in, liquid prior to injection may also be prepared.

The active immunogenic ingredients (the ARPs) are often mixed with excipients or carriers that are pharmaceutically acceptable and compatible with the active ingredient. Suitable excipients include but are not limited to sterile water, saline, dextrose, glycerol, ethanol, or the like and combinations thereof.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic product of the ARP resulting from administration of the immunogen in vaccines which are also comprised of the various adjuvants. Such additional formulations and modes of administration as are known in the art may also be used.

One or more immuno-potentiator molecules, such as chemokines and/or cytokines, can be incorporated into the immunogenic composition administered to the patient or animal. Alternatively, alphavirus replicon vectors which contain coding sequence(s) for the immuno-potentiator molecule can be incorporated in the immunogenic composition. It is understood that the choice of chemokine and/or cytokine may vary according to the neoplastic tissue or cell, parasite or pathogen against which an immune response is desired. Examples can include, but are not limited to, interleukin-4, interleukin-12, gamma-interferon, granulocyte macrophage colony stimulating factor and FLT-3 ligand.

The immunogenic (or otherwise biologically active) ARP-containing compositions are administered in a manner compatible with the dosage formulation, and in such amount as will be prophylactically and/or therapeutically effective. The quantity to be administered, which is generally in the range of about $10^1$ to about $10^{10}$ infectious units, preferably $10^5$ to $10^8$, in a dose, depends on the subject to be treated, the capacity of the individual's immune system to synthesize antibodies, and the degree of protection desired. Precise amounts of the active ingredient required to be administered may depend on the judgment of the physician, veterinarian or other health practitioner and may be peculiar to each individual, but such a determination is within the skill of such a practitioner.

The vaccine or other immunogenic composition may be given in a single dose or multiple dose schedule. A multiple dose schedule is one in which a primary course of vaccination may include 1 to 10 or more separate doses, followed by other doses administered at subsequent time intervals as required to maintain and or reinforce the immune response, e.g., at weekly, monthly or 1 to 4 months for a second dose, and if needed, a subsequent dose(s) after several months or years.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) Molecular Cloning, Second Edition, Cold Spring Harbor Laboratory, Plainview, N.Y.; Maniatis et al. (1982) Molecular Cloning, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering Principles and Methods*, Vols. 1-4, Plenum Press, New York; and Ausubel et al. (1992) *Current Protocols in Molecular Biology*, Greene/Niley, New York, N.Y. Abbreviations and nomenclature, where employed, are deemed standard in the field and commonly used in professional journals such as those cited herein.

All references cited in the present application are incorporated by reference in their entireties to the extent that they are not inconsistent with the present disclosure.

The following examples are provided for illustrative purposes, and are not intended to limit the scope of the invention as claimed herein. Any variations in the exemplified articles which occur to the skilled artisan are intended to fall within the scope of the present invention.

EXAMPLES

Example 1

Generation of Alphavirus Replicon Vectors Expressing a Library of Tumor Associated Antigens Tumor cells are typically obtained from a cancer patient by resection, biopsy, or endoscopic sampling; the cells may be used directly, stored frozen, or maintained or expanded in culture RNA is extracted from tumor cells using standard methods known in the art, e.g. using commercially available reagents and kits such as Trizol (Sigma, St. Louis, Mo.) or S.N.A.P. total RNA isolation kit (Invitrogen, Inc, Carlsbad, Calif.), followed by mRNA purification on oligo (dT)-Sepharose. mRNA can be further enriched in tumor-specific sequences by subtractive hybridization or other method known in the art. First-strand cDNA is synthesized using oligo (dT) oligonucleotides with a rare restriction site at 5'-terminus. Following purification of the cDNA, the second strand is produced using any of the standard methods, e.g. using DNA polymerase I-RnaseH or non-specific amplification. An adaptor is then ligated to create a cohesive end, and double-stranded DNA is digested with a rarely recognized restriction endonuclease (such as DraI) at a site which has been incorporated in the oligo (dT) primer. This procedure creates a double-stranded cDNA with non-compatible cohesive ends suitable for directional cloning.

Alternatively, a strategy described in Example 2 (below) can be used for generation of cohesive ends for directional cloning. In an additional embodiment, cohesive ends can be attached by terminal deoxyribonucleotide transferase. The double-stranded cDNA is then cloned into a plasmid replicon vector or used to construct recombinant replicon molecules in vitro in a manner similar to the one described below. This approach produces recombinant replicon molecules that contain a biotin label on the 3'-termini and a T7 promoter on the 5'-termini, thus allowing for selection of the recombinant molecules and generation of RNA in vitro using T7 DNA-dependent RNA polymerase. Additional selective steps can be implemented to "down-select" the number of antigens present in the tumor antigen library. Methods such as subtractive hybridization and differential analysis are well known in the art (See U.S. Pat. Nos. 5,958,738, 5,827,658 and 5,726,022 and U.S. Patent App. 2002-0018766), and such a selection method can be implemented immediately prior to cloning into the VEE replicon construct. This approach serves to limit the tumor antigen pool to genes either exclusively expressed or preferentially up-regulated in a tumor cell. This selection serves to reduce or eliminate the frequency and/or presence of normal cellular genes in the antigen library. Without wishing to be bound by any particular theory, it is believed that additional benefits include the elimination of non-tumor specific antigens focusing of the immune response against tumor-associated antigens, thus maximizing the potential specificity of the vaccine preparation and reducing the risk of inducing autoimmune responses. This "down-selection" of the antigen repertoire is also relevant to prime-boost strategies. In many instances, it may be advantageous to vaccinate with a broad array of tumor antigens, and in the subsequent boost inoculations, to limit/down-select the number of antigens so as to effectively focus the immune system on specific antigens. This can feasibly be done by down-selecting antigens also based on identifying which antigens the host has responded to following the first immunization, and thus essentially tailoring each subsequent boost to augment the immune response to antigens the host has demonstrated it can recognize and to which an immune response has been raised.

Example 2

Generation of Alphavirus Replicon Vectors Expressing cDNAs Specific for Infectious Disease Organism from a Sample of Infected Tissue or Blood when the Target Gene Sequences are Known This example describes cloning of a viral/bacterial/parasitic gene repertoire specific for an individual with either an acute or chronic infection in instances where the gene or genes of interest (i.e., the genes which encode the immunogenic moieties to be expressed by the replicons) are acquired from an agent of known sequence. An mRNA is isolated from a tissue or blood sample following standard methods known in the art, e.g. S.N.A.P. total RNA isolation kit (Invitrogen, Inc. Carlsbad, Calif.). First-strand cDNA is synthesized by any standard methods known in the art, e.g. cDNA cycle kit (Invitrogen, Inc, Carlsbad, Calif.), or using AMV reverse transcriptase and random primers. The gene(s) of interest are amplified from cDNA using target gene-specific primers, following which the amplicon is purified using a PCR purification kit (Qiagen Inc., Valencia, Calif.) or any other method known in the art. This amplicon can be cloned into the VEE replicon using methods known to those skilled in the art, e.g. using G:C cloning, directional cloning following restriction endonuclease digestion or in vitro recombination methods such as Gateway (Invitrogen, Carlsbad, Calif.) or the Cre-lox recombination system.

In a preferred embodiment, the coding sequence(s) of interest are amplified using RNA/DNA hybrid oligonucleotides. Following amplification, the DNA amplicon is treated with NaOH to digest the RNA portion of the primers, or alternatively, incubated at 50° C. in the presence of rare-earth metals to selectively hydrolyze the phosphodiester bond between the deoxyribonucleotide and the ribonucleotide (Chen et al., 2000, Biotechniques; 28(3):498-500, 504-5 and Chen et al., 2002, *Biotechniques*, 32:516, 518-20) in order to create a 3'-overhang required for ligation. A complementary 3'-overhang in the vector sequences is created in a similar fashion or by using a restriction endonuclease. In this manner the two fragments of the replicon molecule are prepared: the left arm and the right arm. The left arm includes a T7 promoter operatively linked to VEE specific sequences, up to and including a convenient cloning site. The right arm contains the 3'-untranslated region of VEE. The right arm also contains a biotin label at the 3'-terminus. The amplified fragment with a 3'-overhang is linked to the left and right arms of the vector using T4 DNA ligase. The assembled molecule is separated from the ligation reaction mixture using magnetic streptavidin-coated beads, or any other similar solid-phase absorption technique. Full-length replicon RNA is produced from purified recombinant vector DNA by in vitro transcription using T7 DNA-dependent RNA polymerase. This step results in production of only full-length recombinant molecules, since incomplete molecules do not bind to streptavidin, or are not transcribed due to the lack of T7 promoter sequences. The resulting recombinant replicon RNA molecules encode a comprehensive repertoire of the target gene(s), which represent the genotype of the target which is infectious in the patient. An advantage of this method is the ability to have representation of all variants for a particular gene population from an individual, e.g. amplification of the HIV-1 envelope gp160 gene sequence isolated from an HIV-infected patient using the methods outlined above generates an ARP population encoding the majority or all of the envelope variants from that particular patient. If the patient is infected with multiple strains of virus or distinct variants originating from an original parental circulating strain, the technique above captures all variants and they are represented in the final ARP vaccine population.

Example 3

Generation of Alphavirus Replicon Vectors Expressing Infectious Disease Specific cDNA from a Sample of Infected Tissue/Blood when the Target Gene Sequences are not Known This example describes cloning of a viral/bacterial/parasitic gene repertoire in cases where the gene or genes of interest are not of a known sequence. Viral, bacterial or parasitic mRNA is isolated from a field sample or a stock culture or purified preparation using MICROBExpress kit (Ambion, Austin, Tex.) or any other method known to those skilled in the art. First strand cDNA is synthesized using random primers, or random primers with a rare restriction site at the 5'-terminus, followed by second-strand cDNA synthesis with DNA polymerase I and RNase H using standard methods known to one skilled in the art. Double-stranded cDNA is subsequently cloned into a VEE vector after ligation of an adaptor or a linker sequence as follows. In cases when the cDNA is synthesized with a random primer containing a rare restriction site, a linker is used to attach a second different rare restriction site at the 5'-terminus of double-stranded cDNA. Digestion of the cDNA pool with these two restriction endonucleases results in the generation of cDNA fragments with different cohesive ends, which facilitates directional cloning into the replicon vector using methods known in the art. In the case that cDNA is generated with a random primer lacking an additional unique restriction site, double-stranded cDNA is methylated using EcoRI methylase to protect internal sequences from subsequent digestion with EcoRI restriction enzyme. The EcoRI linker is then attached using T4 DNA ligase, followed by digestion with EcoRI restriction endonuclease. This produces a cDNA fragment with cohesive ends, which can be cloned into a replicon. A cloning strategy similar to the one described in Example 2 can be used for the generation of a pool of replicon molecules labeled with biotin at the 3'-terminus and containing a T7 DNA-dependent RNA polymerase promoter at the 5'-terminus. Again, as described in the previous examples, subtractive hybridization or differential display can be used as additional subsequent screening steps to positively or negatively select pathogen specific genes/sequences in a manner similar to that described for the tumor specific approaches. Again, this can be done with all vaccinations or on a "real-time" basis where the host is monitored during vaccinations and the vaccine is tailored to contain antigens to which the host demonstrates recognition and response.

Example 4

Multi-Antigenic ARP Packaging

Generation of a population of ARPs in which each ARP expresses a different antigen or antigens from a single electroporation event were performed in two alternate manners. The first method consisted of combining 0.5 µg of DNA from 10 different replicon vector constructs, each containing a single heterologous coding sequence (Table 1). The DNAs were linearized with NotI restriction enzyme, and RNA was transcribed from the replicon DNA pool with T7 RNA polymerase. The multiple-replicon RNA transcription reaction was then purified using an RNEasy column (Qiagen Inc., Valencia, Calif.). ARP were produced by electroporation using 30 µg of multiple-replicon RNA combined with 30 µg each of purified capsid (C) helper and glycoprotein (GP) helper RNAs into $1.0 \times 10^8$ Vero cells in a 0.8 mL volume cuvette. After electroporation, the cells were suspended in 200 mL of Opti-pro media (Invitrogen, Carlsbad, Calif.) and seeded into 4, 175 cm² culture flasks. Approximately 26 hr post electroporation the media from each flask was discarded and replaced with 5 mL of a salt wash solution (1 M NaCl in 20 mM phosphate buffer (pH 7.3). The flasks were incubated at room temperature for 10 minutes, the salt wash was collected and filtered through a 0.2 micron syringe filter. The titer of individual ARP was determined in Vero cells using antigen-specific antibodies by standard immunofluorescence methods. The titer of each ARP in the pool produced from a single electroporation is shown in Table 1. The titer of the ARP preparation was $4.1 \times 10^9$ infectious units per mL, resulting in a total of $8.2 \times 10^{10}$ i.u. total ARP generated from a single cuvette electroporation. Representatives of all 10 antigens were present in the ARP population. This example demonstrates that not only can multiple different antigens be expressed from a single ARP preparation, but that the range of antigen type can be extremely varied. In this preparation antigens were derived from viral infectious disease origin (HIV), from parasitic origin (malaria), or from cancer origins (rat/Neu and cancer antigen A) as well as enzymes (CAT, luciferase and β-gal).

The second method consisted of generating RNA transcripts for each replicon vector independently rather than as a pool. The 7 replicon vectors used in this experiment are listed in Table 2. 10 µg of each purified replicon RNA was combined with 30 µg each of purified C-helper and GP-helper RNAs for a total of 130 µg of RNA. The RNA mix was then electroporated into $1.0 \times 10^8$ Vero cells. Electroporated cells were suspended in 200 mL of Opti-pro media and seeded into 2 300 cm² culture flasks. Approximately 24 hr post electroporation the media from each flask was collected and replaced with 10 mL of salt wash (1 M NaCl in 20 mM phosphate buffer, pH 7.3). The flasks were incubated at room temperature for 5 minutes, and the salt wash was collected. Both the media and salt wash material were filtered through a 0.2 micron syringe filter. The individual ARP in both the media and salt wash were titrated in Vero cells using antigen specific antibodies for IFA. The titer of each ARP found in either the media or salt wash is shown in Table 2. The titer of the ARP recovered in the media was $5.3 \times 10^7$ i.u./mL resulting in $1.1 \times 10^{10}$ i.u. total ARP generated ($5.3 \times 10^7$ i.u./mL$\times$200 mL=$1.1 \times 10^{10}$ i.u.). The titer of the ARP recovered in the salt wash was $4.05 \times 10^9$ i.u./mL resulting in $8.1 \times 10^{10}$ i.u. total ARP generated per single cuvette electroporation. The material in the salt wash and the media were combined for a total of $9.2 \times 10^{10}$ i.u. ARP. Representatives of all 7 antigens were present in the ARP population. The pooled ARP were then purified on a HiTrap Heparin HP 5 mL column (Amersham Bioscience, Uppsala, Sweden) for use in animal vaccination studies.

ARP preparations were all evaluated by standard safety testing to confirm the absence of replication competent virus (RCV). Briefly, $1 \times 10^8$ i.u. of each preparation was inoculated onto VERO cell monolayers at an m.o.i. of less than 1 for 1 hour. Growth media was applied to the cell monolayers after a 1 hour infection period and cells cultured for 24 hours. After 24 hours, the entire supernatant was harvested, clarified and applied to fresh VERO cell monolayers for a further 48 hours. Cell monolayers were monitored for the presence of any cytopathic effect (CPE) indicative of the presence of contaminating replication competent virus particles. In all cases, no RCV was detected in any multi-antigenic ARP vaccine preparations.

Example 5

Animal Studies with Multi-Antigenic Virus Particles

Five to six week-old female BALB/c mice were obtained from Charles River Laboratories and were acclimatized for one week prior to any procedure. Mice were fed ad libitum water (reverse osmosis, 1 ppm Cl) and an irradiated standard rodent diet (NIH31 Modified and Irradiated) consisting of 18% protein, 5% fat, and 5% fiber. Mice were housed in static microisolators on a 12-hour light cycle at 21-22° C. (70-72° F.) and 40%-60% humidity. All animal studies comply with recommendations of the Guide for Care and Use of Laboratory Animals with respect to restraint, husbandry, surgical procedures, feed and fluid regulation, and veterinary care. The animal care and use program is AAALAC accredited.

For prime and boost injections, groups of mice were each inoculated in both rear footpads under isoflorane anesthesia with multi-antigenic ARP in diluent (PBS with 1% v/v human serum albumin and 5% w/v sucrose). Footpad subcutaneous (s.c.) injections were performed with a 30.5 G needle and a 0.10 mL Hamilton syringe by injecting 20 μL in each footpad. Intraperitoneal (i.p.) inoculations were administered by the same syringe/needle but in a volume of 0.1 mL. Animals were inoculated on days 1, 23 and 44. Serum samples were obtained by retro-orbital bleeding under isoflorane anesthesia before the first inoculation on days—7 and 0 (pre-bleed), days 30 and 35 (after the primary inoculation) and days 51 and 56 (7 and 12 days after the boost). Spleens were harvested at least 7 days post-boost for IFN-γ ELISPOT assays.

Immunofluorescence assay (IFA) of ARP-infected Vero cells was used to measure the potency or infectious titer of each of the vaccine preparation. All ARP vaccines were titered prior to inoculations. On the day of each injection residual inocula were back-titrated. ARP vaccine inocula were kept at 4° C. during the time following vaccination to maintain titer. Test groups included the following vaccine preparations: high and low dose multi-antigenic ARP preparations administered as dosages of $1\times10^8$ or $1\times10^6$ i.u., respectively. As a control for monitoring the immune response as compared to a single ARP preparation expressing a single antigen ARP expressing HIV Gag alone were administered at a dosage equivalent to the number of HIV-Gag ARP in the multi-antigenic mix. Negative control animals were sham immunized with diluent alone.

Example 6

Measurement of Humoral and Cellular Immune Responses after Multi-Antigenic ARP Administration Detection of HIV Gag specific antibodies by ELISA. Purified recombinant histidine-tagged (his)-p55 from HIV-1 subtype C isolate DU-422 was used as antigen coat. Briefly, BHK cells were transfected with VEE replicon RNA expressing his-p55 and Triton-X 100 lysates were prepared. Protein was purified by ion metal affinity chromatography, in accordance with the suppliers' recommendations.

Sera from Day 51 (7 days post boost) were evaluated for the presence of Gag-specific antibodies by a standard indirect ELISA. For detection of Gag-specific total Ig, a secondary polyclonal antibody that detects IgM, IgG and IgA was used for end point titer determination. Briefly, 96-well Maxisorp ELISA plates (polystyrene multiwell plates with modified surface to increase affinity for polar molecules, i.e., antibodies; Nunc, Naperville, Ill.) were coated with 50 μL of 0.05 M sodium carbonate buffer, pH 9.6 (Sigma, St. Louis, Mo.) containing 40-80 ng his-p55 per well. Plates were covered with adhesive plastic and incubated overnight at 4° C. The next day, unbound antigen was discarded and plates were incubated for 1 hour with 200 μL blocking buffer (PBS containing 3% w/v BSA) at room temperature. Wells were washed 6 times with PBS and 50 μL/well of test serum, diluted serially two-fold in buffer (PBS with 1% w/v BSA and 0.05% v/v Tween 20), was added to antigen-coated wells. Mouse anti-p24 monoclonal antibody (Zeptometrix, Buffalo, N.Y.) was included in every assay as a positive control. Negative controls in each assay included blanks (wells with all reagents and treatments except serum) and pre-bleed sera. Plates were incubated for one hour at room temperature, and then rinsed 6 times with PBS. 50 μL/well of alkaline phosphatase (AP)-conjugated goat anti-mouse poly-isotype secondary antibody (Sigma) diluted to a predetermined concentration in diluent buffer was added to each well and incubated for 1 hour at room temperature. Wells were rinsed 6 times with PBS before addition of 100 μL p-nitrophenyl phosphate (pNPP) substrate (Sigma). The serum antibody ELISA titer was defined as the inverse of the greatest serum dilution giving an optical density at 405 nm greater than or equal to 0.2 above the background (blank wells). Positive antibody (immune) responses were detected in mice vaccinated with the multi-antigenic ARP preparation and in mice that received the ARP HIV-Gag.

Gag and Pol antigen-specific Interferon-gamma (IFN-γ) secreting cells are detected by IFN-γ ELISPOT Assay. Single-cell suspensions of splenic lymphocytes from ARP-immunized BALB/c mice were prepared by physical disruption of the splenic capsule in R-10 medium (RPMI medium 1640 supplemented with 100 U/mL penicillin, 100 μg/mL streptomycin, 0.1 mM MEM non-essential amino acids solution, 0.01 M HEPES, 2 mM glutamine and 10% heat inactivated fetal calf serum). Lymphocytes were isolated by Lympholyte M density gradient centrifugation (Accurate Scientific, Westbury, N.Y.), washed twice and resuspended in fresh R-10 medium. Total, unseparated splenic lymphocyte populations were tested.

A mouse IFN-(ELISPOT kit (Monoclonal Antibody Technology, Nacka, Sweden) was used to perform the assay. Viable cells were seeded into individual ELISPOT wells in a Multiscreen Immobilon-P ELISPOT plate (ELISPOT certified 96-well filtration plate with high protein-binding PVDF membranes; Millipore, Billerica, Mass.) that had been pre-coated with an anti-IFN-(monoclonal antibody, and incubated for 16-20 hours. Cells were removed by multiple washes with buffer and the wells were incubated with a biotinylated anti-IFN-(monoclonal antibody, followed by washing and incubation with Avidin-Peroxidase-Complex (Vectastain ABC Peroxidase Kit, Vector Laboratories, Burlingame, Calif.). Following incubation, the wells were washed and incubated for 4 minutes at room temperature with substrate (Avidin-Peroxidase Complex tablets, Sigma, St. Louis, Mo.) to facilitate formation of spots, which represent the positions of the individual IFN-(-secreting cells during culture. Plates were enumerated by automated analysis with a Zeiss KS ELISPOT system.

To enumerate Gag-specific IFN-γ secreting cells in lymphocytes from mice immunized with HIV GAG ARP and multi-antigenic HIV ARP constructs expressing gag, lymphocytes were stimulated with the immunodominant CD8H-2K$^d$-restricted HIV-Gag peptide, or an irrelevant Nef peptide pool (Nef peptide containing 10 15-mers overlapping by 11 made from Clade C HIV strain $DU_{151}$), for 16-20 hours (5% $CO_2$ at 37° C.). The Gag peptide was tested at 10 μg/mL and the Nef control was tested at 20 μg/mL. Cells minus peptide serve as a background control. As a positive control, cells were stimulated with 4 μg/mL concanavalin A for a similar time period. Peptides were synthesized and purified to >90% (New England Peptide, Gardner, Mass.).

To enumerate Pol-specific IFN-(secreting cells in lymphocytes from mice immunized with multi-antigenic ARP constructs expressing pol, the protocol above was used with the following modifications. HIV-1 Pol epitopes for both CD8 and CD4 T cells have been recently identified in the H-$2^d$ background (Casimiro et al., *J. Virology* 76:185, 2002). Cell populations were stimulated with a pool of 3 Pol epitope-containing peptides and with an irrelevant antigen peptide pool as a negative control (nef pool 1). The three peptides below were selected after a literature search to identify the known murine Pol CTL epitopes.

```
VYYDPSKDLIA (SEQ ID NO: 1)  (Casimiro et al, J.
                             Virol. 76: 185, 2002)

ELRQHLLRWGL (SEQ ID NO: 2)  (Casimiro et al, J.
                             Virol. 76: 185, 2002)

ELREHLLKWGF (SEQ ID NO: 3)  (homologue to number 2,
                             identical to our se-
                             quence).
```

These three peptides were mixed together at a concentration of 10 μg/mL each (total peptide concentration was 30 μg/mL) and added to triplicate wells. The ELISPOT assay results presented were performed 26 days post the second boost.

Detection of Rat/neu specific antibodies was by ELISA. Rat/neu antigen for use as an ELISA reagent was prepared as follows: a histidine tag was added by PCR to the C-terminus of the Rat/neu coding sequence in pRAT/neu #14. This PCR amplified product was digested and ligated into the VEE replicon plasmid, pERK. BHK cells were electroporated with RNA generated from the pERK Rat/neu-his construct. At 16 hours post-electroporation cell lysates were prepared and purified over a nickel affinity column, achieving 60-70% purity of the his-tagged Rat neu antigen.

Sera from Day 51 (7 days post boost) were evaluated for the presence of Rat/neu-specific antibodies by an indirect ELISA. Nunc high binding plates were coated at 4° C. overnight with 75 ng/well of his-tagged Rat neu in carbonate-bicarbonate coating buffer. The next day plates were blocked with 200 μl/well of 3% BSA in PBS for 1 hour at 30° C. After 6 washes in PBS, 50 μl of mouse serum samples were diluted in 1% BSA, 0.05% Tween 20 in PBS and added to each well and the plates were incubated for 1 hr at 30° C. Pre-bleeds at 1:40 and 1:80, as well as two-fold dilutions from 1:40-1:1280 of day 51 sera were tested for each experimental animal. Plates were then washed 6 times with PBS, followed by the addition of 50 μl/well of a 1:500 dilution of goat anti-mouse HRP and incubated for 1 hr at 30° C. Plates were washed as before and developed with 100 μl/well of ABTS (KPL), and the absorbance was read at 405 nm using a standard ELISA reader. The cut off value to determine a positive sample was determined by averaging the OD (absorbance) value of all the pre-bleed serum samples diluted 1:40 and multiplying that value by two. Any sample with an OD greater than the cut off value was considered positive.

Detection of anti-CAT specific antibodies was by ELISA. An anti-CAT antibody ELISA was developed to detect anti-CAT immune responses in multi-antigen ARP vaccinated mice. ELISA microplates coated with sheep anti-CAT polyclonal antibodies (Roche, Indianapolis, Ind.) were loaded with 0.15 ng of purified CAT protein suspended in CAT ELISA sample buffer (Roche) in a volume of 50 μl per well. The ELISA plates were incubated at 37° C. for 45 min and washed three times with 0.2 mL of CAT ELISA wash buffer (Roche). 50 μl of mouse serum, two-fold serially diluted in sample buffer, was loaded per well and the plates were incubated at 37° C. for 45 min. After incubation, the ELISA plates were washed three times as described above. Goat anti-mouse HRP-conjugated secondary antibody (Kirkegaard and Perry Laboratories (KPL), Gaithersburg, Md.) diluted 1:500 in sample buffer was added to each well (0.1 mL per well) and incubated at 37° C. for 45 min. After incubation, the plates were washed three times as described above, and 0.1 mL of ABTS peroxidase substrate (2,2'-azino-bis 3-ethylbenzthiazoline-b-sulfonic acid; KPL) was added per well. Color development was ended by addition of 0.1 mL stop solution (KPL) and the absorbance in the plates were read at 405 nm using a Molecular Devices Versamax microplate reader. The cut off value to determine a positive sample was determined by averaging the OD value of all the pre-bleed serum samples diluted 1:40 and multiplying that value by two. Any sample with an OD greater than the cut off value was considered positive.

Detection of CMV gB specific antibodies was by Western blot. Analysis of anti-gB immune responses in multi-antigen ARP vaccinated animals was by Western blot. Purified, recombinant, histidine-tagged gB protein was electrophoresed through 4-10% Bis-Tris NuPAGE gels (Sodium dodecyl sulfate-polyacrylamide gel; Invitrogen, Carlsbad, Calif.) and transferred to PVDF membranes using a Novex mini-cell (Invitrogen) electrophoresis unit. Pre-bleed and Day 51 post-vaccination sera were diluted 1:40 or 1:80 for each animal in blocking buffer (Invitrogen) and incubated on strips of PVDF membranes after gB protein transfer. Goat anti-mouse alkaline phosphates conjugated antibody (Sigma, St. Louis, Mo.) diluted 1:10,000 in blocking buffer was used as the secondary antibody. Western blots were developed using BCIP/NBT (5-bromo,4-chloro,3-indolylphosphate/nitroblue tetrazolium; Bio Rad, Hercules, Calif.), and color development was arrested by washing with distilled water. Positive samples were identified by visual detection of immunoreactive bands with electrophoretic mobility matching the expected molecular weight of gB on the immunoblot.

Detection of Influenza HA specific antibodies was by immunofluorescence assay (IFA). Analysis of anti-HA immune responses in multi-antigen ARP vaccinated animals was determined by IFA. Vero cells were electroporated with a VEE replicon vector that expressed the H1N1 influenza HA gene and $1 \times 10^4$ electroporated cells per well were seeded into 96 well tissue culture plates. Electroporated Vero cells were fixed with methanol 16 hr post-electroporation. Pre-bleed and day 56 post-vaccination sera were diluted two-fold from 1:40 to 1:160 in blocking buffer (PBS:FBS (1:1)) for each animal and incubated on HA protein expressing Vero cells. A goat anti-mouse Alexa Fluor 488 conjugated antibody (Molecular Probes, Eugene, Oreg.) diluted 1:400 was used as the secondary antibody. Cells were analyzed on a Nikon Eclipse TE300 UV microscope for HA specific fluorescence. Titer was determined by visual detection of immunofluorescent cells at the lowest detectable serum dilution value.

Detection of anti-CMV IE1 specific antibodies was by ELISA. Purified recombinant histidine-tagged (his)-IE1 from CMV was used as antigen coat. Briefly, BHK cells were transfected with VEE replicon RNA expressing his-IE1 and Triton-X 100 lysates were prepared. Protein was purified by ion metal affinity chromatography.

Sera from Day 51 (7 days post boost) were evaluated for the presence of CMV-IE1-specific antibodies by a standard indirect ELISA. For detection of CMV-IE1-specific total Ig, a secondary polyclonal antibody that detects IgM, IgG and IgA was used for end point titer determination. Briefly, 96-well Maxisorp ELISA plates (Nunc, Naperville, Ill.) were coated with 2 µg IE1 in a volume of 50 µL in citrate/phosphate, pH 8.3, per well. Plates were covered with adhesive plastic and incubated overnight at 4° C. The next day, unbound antigen was discarded and plates were incubated for 1 hour with 200 µl blocking buffer (PBS containing 3% w/v BSA) at room temperature. Wells were washed 6 times with PBS and 50 µl of serum, diluted serially two-fold in buffer (PBS with 1% w/v BSA and 0.05% v/v Tween 20), was added to antigen-coated wells. An α-IE1 monoclonal antibody (Rumbaugh-Goodwin Institute for Cancer Research, Inc, Plantation, Fla.) was included in every assay as a positive control. Negative controls in each assay included blanks (wells with all reagents and treatments except serum) and pre-bleed sera. Plates were incubated for one hour at room temperature, and then rinsed 6 times with PBS. Fifty µL/well of alkaline phosphatase (AP)-conjugated goat anti-mouse poly-isotype secondary antibody (Sigma) diluted to a predetermined concentration in diluent buffer was added to each well and incubated for 1 hour at room temperature. Wells were rinsed 6 times with PBS before addition of 100 µl p-nitrophenyl phosphate (pNPP) substrate (Sigma). The serum antibody ELISA titer was defined as the inverse of the greatest serum dilution giving an optical density at 405 nm greater than or equal to 0.2 above the background (blank wells).

Summary of Immune Response to Multi-Antigenic ARP

As shown in FIG. 1 and Table 3, animals vaccinated with multi-antigenic ARP mounted immune responses to all seven antigens present in the ARP population. These immune responses included both humoral and cellular responses, indicating this type of approach can stimulate both arms of the immune system. The strength of the immune response to a specific antigen was also measured in the context of the multi-antigenic ARP and compared to a single-antigen ARP preparation. Anti-Gag antibody and cellular immune responses were equivalent whether the HIV-Gag ARP was alone or in a multi-antigenic formulation, indicating that addition of a plurality of different antigens does not appear to diminish the immune response to each individual component of the preparation. This multi-antigenic preparation was intentionally composed of genes from infectious disease agents (HIV and CMV), cancer antigen (Rat/neu) and bacterial enzyme (CAT) to demonstrate that the host immune system can be stimulated with multi-antigenic ARP to respond to a broad array of antigen types within a single ARP preparation.

Example 7

Animal Studies with Multi-Antigenic ARPs Expressing a Tumor cDNA Library

A cDNA library is generated from a B16F10 (B16) [Gold et al., (2003) *J. Immunol.* 170:5188-5194) pigmented mouse melanoma cell line originally derived from C576BL/6 mice. This library is directionally cloned into the alphaviral replicon cDNA construct so that the heterologous cDNA is expressed from the replicon upon infection of a target cell. ARP are generated and purified as described above to produce a population of ARP particles expressing an entire library of cDNAs from the B16 tumor cells. Expression of representative genes such as β-actin can be analyzed by quantitative PCR to determine whether the library expresses known gene standards. Subtractive hybridization or differential display against a non-tumorigenic genetically matched cell line can be used to enhance the proportion of tumor-specific sequences in the library.

C57BL/6 mice are vaccinated with the B16 library ARP preparation one, two or three times on days 0, 21 and 42. Doses of between $10^5$-$10^9$ i.u. in ARP are administered via a subcutaneous (sc.) route delivered both rear footpads of the mouse. Control groups of mice receive placebo vaccinations or ARP expressing irrelevant antigens. An additional set of animals can be included which receive ARP expressing single known melanoma specific tumor antigens such as TYR, TRP-2, gp100, MAGE-1 or MAGE-3, or a combination of said antigens as comparators to the multi-antigenic approach.

Mice are injected intradermally (id.) with $10^4$, $10^5$ or $10^6$ B16 melanoma cells on the right flank 5 days after the final ARP immunization. The mice are then followed for tumor onset by palpation every other day. Tumors are scored as present once they reach a diameter of equal to or greater than 2 mm. Mice are sacrificed once it is assured that the tumor is progressing (usually at a size of 1 cm). Kaplan-Meier tumor-free survival curves are constructed and log rank analysis performed to determine statistical significance of protection from tumor challenge between each group.

Prior to tumor challenge, sera and lymphocytes are harvested from mice for immunoassay. The presence of humoral or cellular responses to known tumor antigens expected to be present in the ARP B16 library can be assayed using standard methods and techniques known in the art.

Canine malignant melanoma (CMM) is a spontaneous, aggressive and metastatic neoplasm which occurs in dogs. CMM is a relatively frequently diagnosed tumor and accounts for about 4% of all canine tumors. CMM is initially treated with local therapies including surgery and/or fractionated radiation therapy; however, systemic metastatic disease is a common sequela. CMM is a chemo-resistant neoplasm. All these properties are common to human melanoma, and on the basis of these similarities, CMM serves as a clinical model for evaluating new treatments for human melanoma [Bergman et al. (2003) *Clin. Cancer Res.* 9:1284-1290).

Dogs are screened for the presence of histologically confirmed spontaneous malignant melanoma. Pre-trial evaluation includes complete physical evaluation, complete blood count and platelet count, serum chemistry profile, urinalysis, LDH, anti-nuclear antibody, and three-dimensional measurements of the primary tumor if present (or maximal tumor size from medical records if patient has been treated before pre-trial considerations). For the evaluation of metastatic disease, 3-view radiographs of the thorax are obtained and regional lymph nodes are evaluated with fine needle aspiration/cytology and/or biopsy/histopathology. All dogs are staged according to the WHO staging system of stage II tumors (tumors 2-4 cm diameter, negative nodes), stage III (tumor >4 cm and/or positive nodes) or stage IV (distant metastatic disease). Dogs from all three of these stages of disease are included in the study, provided they have not received any other form of therapy in the previous three weeks.

Fine needle aspiration or biopsy is used to confirm malignant melanoma in each animal by cytology or histopathology, respectively. These samples, taken from either the primary tumor mass or from metastatic masses, are used as the source of the tumor cDNA library. For each animal, tumor RNA is isolated form the tumor cell population. A cDNA library is prepared from each sample. Multi-antigenic ARP preparations are generated for each animal as described herein.

Cohorts of dogs receive multiple vaccinations of canine patient-specific ARP preparations with a range of dosages. Dogs are vaccinated between 3-12 times over a period of 1-3 months. Dosages of ARPs administered via either a subcutaneous, intradermal or intramuscular route range from $10^6$ to $10^9$ i.u. In addition to administering patient-specific (autologous) ARP vaccines, some cohorts can receive ARP preparations from other patients (allogeneic) in order to determine if a vaccine preparation from an alternate melanoma provides clinical benefit.

The clinical status of each patient is monitored throughout the vaccination regime and for up to two years following treatment. Patients are physically, radiologically and biochemically examined on a frequent basis for clinical evidence of tumor presence and progression or regression. If euthanasia is requested by owners in the event of degradation in the quality of life due to advanced disease, a full necropsy is performed with subsequent necropsy examination to determine gross and histopathological status of the tumor at primary and metastatic sites. Statistical analysis is performed to determine the effect of multi-antigenic ARP vaccination on survival and disease progression. Statistical analysis tools include the Kaplan-Meier product limit method, Cox proportional hazard analysis, Mann-Whitney U test, and a Spearman rank correlation.

TABLE 1

Titration of Multi-antigenic ARPs (Pool of 10 constructs)

| Replicon vector | ARP titer |
| --- | --- |
| CAT(chloramphenicol acetyltransferase) | $3.6 \times 10^8$/mL |
| β-gal | $1.3 \times 10^5$/mL |
| Rat/neu | $5.2 \times 10^8$/mL |
| Luciferase | $6.8 \times 10^6$/mL |
| PkMSP1-42 | $4.5 \times 10^8$/mL |
| PyHep17 | $2.0 \times 10^8$/mL |
| PfAMA1 | $4.0 \times 10^7$/mL |
| PkCSP | $5.7 \times 10^8$/mL |
| HIV Gag | $1.5 \times 10^9$/mL |
| Cancer Antigen A | $4.5 \times 10^8$/mL |
| Total/mL | $4.1 \times 10^9$/mL |
| Total from single cuvette electroporation | $8.2 \times 10^{10}$ |

TABLE 2

Titration of Multi-antigenic ARPs Produced from a Pool of Seven RNAs

| Replicon vector | ARP titer in media | ARP titer in salt wash |
| --- | --- | --- |
| CMV IE1 | $2.9 \times 10^6$/mL | $1.9 \times 10^8$/mL |
| CMV gB | $2.9 \times 10^5$/mL | $5.8 \times 10^7$/mL |
| Influenza HA | $1.3 \times 10^5$/mL | $1.9 \times 10^7$/mL |
| HIV pol | $3.4 \times 10^6$/mL | $3.3 \times 10^8$/mL |
| HIV Gag | $4.2 \times 10^7$/mL | $2.9 \times 10^9$/mL |
| Rat/neu | $1.9 \times 10^6$/mL | $2.6 \times 10^8$/mL |
| CAT(chloramphenicol acetyltransferase) | $2.3 \times 10^6$/mL | $2.9 \times 10^8$/mL |
| Total/mL | $5.7 \times 10^7$/mL | $4.1 \times 10^9$/mL |
| Total from single cuvette electroporation | $1.1 \times 10^{10}$ | $8.2 \times 10^{10}$ |
| Total Pooled ARP Titer | | $9.3 \times 10^{10}$ |

TABLE 3

Antigen-specific Immune Responses in Animals Immunized with Multi-antigenic ARPs

| Vaccination Group | HIV GAG ELISA | HIV GAG ELISPOT | HIV POL ELISPOT | FLU HA IFA | CMV gB Western | CAT ELISA | Rat/neu ELISA | CMV IE1 ELISA |
| --- | --- | --- | --- | --- | --- | --- | --- | --- |
| Multi-Ag ARP s.c. footpad | 8192 | 475 | 614 | 160[a] | 80[a] | 1280[a] | 1280[a] | 1280 |
| Multi-Ag ARP i.p. | 40960[a] | 439 | 105 | 160[a] | 80[a] | 1280[a] | 320 | 2560[a] |
| HIV GAG ARP s.c. footpad | 5120 | 500 | 0[b] | 10[b] | 10[b] | 10[b] | 10[b] | 10[b] |
| Negative control s.c. footpad | 10[b] | 0[b] | 0[b] | 10[b] | 10[b] | 10[b] | 10[b] | 10[b] |

[a] Samples not tested to full endpoint, actual titers are all equal or greater than this measurement
[b] At or below limit of detection of the assay

REFERENCES CITED IN THE PRESENT APPLICATION

Casimiro D R, Tang A, Perry H C, Long R S, Chen M, Heidecker G J, Davies M E, Freed D C, Persaud N V, Dubey S, Smith J G, Havlir D, Richman D, Chastain M A, Simon A J, Fu T M, Emini E A, Shiver J W. Vaccine-induced immune responses in rodents and nonhuman primates by use of a humanized human immunodeficiency virus type 1 pol gene. *J. Virology.* 2002. 76:185-195, 2002

Chen G J, Qiu N, Karrer C, Caspers P. and Page M G. Restriction site-free insertion of PCR products directionally into vectors. *Biotechniques.* 2000; 28(3):498-500, 504-5.

Chen G J, Qiu N, Page M P. Universal restriction site-free cloning method using chimeric primers. *Biotechniques.* 2002; 32(3):516, 518-20.

Heiser, A., Coleman, D., Dannull, J., Yancy, D., Maurice, M., Lallas, C., Dahm, P., Niedzwiecki, D., Gilboa, E. and J. Vieweg. *J. Clinical Investigation.* 2002. 109(3):409-417.

Kumamoto, T., Huang, E., Paek, H-J., Morita, A., Matsue, H., Valentini, R., and A. Takashima. *Nature Biotechnology.* 2002. 20:64-69.

Rayner, J O, Dryga, S. A. and Kurt I. Kamrud. Alphavirus vectors and vaccination. *Rev. Med. Virol.* 2002. 12:279-296.

Sadanaga N Nagashima H Mashino K, Tahara K, Yamaguchi H Ohta M, Fujie T. Tanaka F. Inoue H. Takesako K, Akiyoshi T. Mori M. Dendritic cell vaccination with MAGE peptide is a novel therapeutic approach for gastrointestinal carcinomas. *Clin. Cancer Res.* 2001 August; 7(8):2277-84.

Yamanaka, R., Zullo, S. A., Tanaka, R., Blaese, M., and K. G. Xanthopoulos. Enhancement of antitumor immune response in glioma models in mice by genetically modified dendritic cells pulsed with Semliki forest virus-mediated complementary DNA. *J. Neurosurg.* 2001. 94(3):474-81.

Ward S. Casey D, Labarthe M C, Whelan M, Dalgleish A, Pandha H. Todryk S.

Immunotherapeutic potential of whole tumour cells. *Cancer Immunol. Immunother.* 2002. 51(7):351-7.

Ying, H., Zaks, T. Z. Rong-Fu, W., Irvine, K. R., Kammula, U.S. Marincola, F. M. Leitner, W. W. and N. P. Restifo. Cancer therapy using a self-replicating RNA vaccine. *Nature Medicine.* 1999. 7(5):823-827

What is claimed is:

1. A method for preparing heparin-binding Venezuelan equine encephalitis virus (VEE) replicon particles (VRPs) encoding and expressing a plurality of antigens of a neoplastic cell, pathogen or parasite, said method comprising the steps of:

a) introducing a plurality of modified Venezuelan equine encephalitis virus (VEE) replicon nucleic acids into a plurality of cells, wherein said cells are permissive for VEE replication and packaging, wherein said modified VEE replicon nucleic acids comprise at least a virus packaging signal and at least one antigen coding sequence of a neoplastic cell, pathogen or parasite expressible in said modified VEE replicon nucleic acids and wherein said modified VEE replicon nucleic acids lack a coding sequence for at least one VEE structural protein, wherein said cells comprise at least one helper nucleic acid encoding the at least one VEE structural protein lacking in the modified VEE replicon nucleic acids, and wherein the plurality of modified VEE replicon nucleic acids encode a plurality of antigens of a neoplastic cell, pathogen or parasite, to produce a plurality of modified cells, wherein the step of introducing the nucleic acids is by electroporation of said cells to produce a plurality of modified cells;

b) culturing said plurality of modified cells of step (a) under conditions allowing (i) expression of the at least one helper nucleic acid encoding the structural protein lacked by the modified VEE replicon nucleic acids and (ii) replication of said modified VEE replicon nucleic acids and packaging of said VEE replicon nucleic acids to form heparin-binding VRPs;

c) contacting the modified cells after step (b) with an aqueous solution having a salt concentration from 0.2M to 5M to release the heparin-binding VRPs into the aqueous solution to produce a VRP-containing solution; and d) collecting VRPs from the VRP-containing solution of step (c).

2. The method of claim 1, wherein the cells are electroporated at a density from $5 \times 10^7$ to $5 \times 10^8$ cells per mL.

3. The method of claim 1, wherein the at least one VEE structural protein whose coding sequence is lacking in the VEE replicon nucleic acids is encoded by a nucleic acid sequence stably integrated within the genome of said cell.

4. The method of claim 1, wherein the at least one VEE structural protein whose coding sequence is lacking in the VEE replicon nucleic acids is introduced on at least one VEE helper nucleic acid which encodes a VEE capsid protein capable of binding said modified VEE replicon nucleic acid, and at least one VEE structural glycoprotein, wherein said VEE glycoprotein associates with said modified VEE replicon nucleic acids and said VEE capsid protein, wherein the at least one helper nucleic acid nucleic acid is introduced into the cells together with said modified VEE replicon nucleic acids.

5. The method of claim 1, wherein the at least one VEE structural protein whose coding sequence is lacking in the VEE replicon nucleic acid is encoded by at least two helper nucleic acids wherein each of said two helper nucleic acids encodes at least one VEE structural protein.

6. The method of claim 1, wherein the at least one VEE structural protein whose coding sequence is lacking in the modified VEE replicon nucleic acids is encoded by a VEE helper nucleic acid, and wherein the VEE helper nucleic acid and the modified VEE replicon nucleic acids are RNA molecules.

7. The method of claim 6, wherein the at least one VEE helper nucleic acid is an RNA molecule which is not capped.

8. The method of claim 1, wherein the at least one VEE structural protein whose coding sequence is lacking in the modified VEE replicon nucleic acids is encoded by a VEE helper nucleic acid which is a DNA molecule.

9. The method of claim 1, wherein the electroporation is carried out in an electroporation cuvette and wherein the cells are present at a density from $10^7$ to $5 \times 10^8$ per mL in the electroporation cuvette.

10. The method of claim 1, wherein step (d) is followed by an ion exchange chromatography step or a heparin affinity chromatography step.

11. The method of claim 1, wherein the VEE is an attenuated VEE.

12. The method of claim 11, wherein the attenuated VEE is strain 3014.

13. The method of claim 1, wherein step c) employs an aqueous solution of NaCl, KCl, $MgCl_2$, $CaCl_2$, $NH_4Cl$, $(NH_4)_2SO_4$, $NH_4$Acetate or $NH_4$ Bicarbonate.

14. The method of claim 1, wherein the pathogen is a virus, a bacterium, a yeast, a fungus or a protozoan.

15. The method of claim 14, wherein the virus is an influenza virus, a herpes virus, a parainfluenza virus, respiratory syncytial virus, cytomegalovirus, human papilloma, or human immunodeficiency virus.

16. The method of claim 14, wherein the protozoan is *Plasmodium falciparum.*

17. The method of claim 14, wherein the bacterium is *Mycobacterium tuberculosis.*

18. The method of claim 1, wherein the neoplastic cell is selected from the group consisting of a pancreatic cancer cell, kidney cancer cell, sarcoma cell, neuroblastoma cell, glioma cell, colon cancer cell, melanoma cell, breast cancer cell, ovarian cancer cell and prostate cancer cell.

19. A method for preparing Venezuelan equine encephalitis virus (VEE) replicon particles (VRPs) encoding and expressing a plurality of antigens of a neoplastic cell, pathogen or parasite, said method comprising the steps of:

a) introducing a plurality of modified Venezuelan equine encephalitis virus (VEE) replicon nucleic acids into a plurality of cells, wherein said cells are permissive for VEE replication and packaging, wherein said modified VEE replicon nucleic acids comprise at least a virus packaging signal and at least one antigen coding sequence of a neoplastic cell, pathogen or parasite expressible in said modified VEE replicon nucleic acids and wherein said modified VEE replicon nucleic acids lack a coding sequence for at least one VEE structural protein, wherein said cells comprise at least one helper nucleic acid encoding the at least one VEE structural protein lacking in the modified VEE replicon nucleic acids, and wherein the plurality of modified VEE replicon nucleic acids encode a plurality of antigens of a neoplastic cell, pathogen or parasite, to produce a plurality of modified cells, wherein the step of introducing the nucleic acids is by electroporation of said cells, wherein the cells are electroporated at a density from $5 \times 10^7$ to $5 \times 10^8$ cells per mL, to produce a plurality of modified cells;

b) culturing said plurality of modified cells of step (a) under conditions allowing expression of the at least one helper nucleic acid encoding the structural protein lacked by the modified VEE replicon nucleic acids and replication of said modified VEE replicon nucleic acids and packaging of said VEE replicon nucleic acids to form VRPs;

c) contacting the modified cells after step (b) with an aqueous solution having a salt concentration from 0.2M to 5M to release the VRPs into the aqueous solution to produce a VRP-containing solution; and d) collecting VRPs from the VRP-containing solution of step (c).

* * * * *

UNITED STATES PATENT AND TRADEMARK OFFICE
CERTIFICATE OF CORRECTION

| | |
|---|---|
| PATENT NO. | : 8,617,533 B2 |
| APPLICATION NO. | : 12/116031 |
| DATED | : December 31, 2013 |
| INVENTOR(S) | : Smith et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 724 days.

Signed and Sealed this
Twenty-first Day of July, 2015

Michelle K. Lee
*Director of the United States Patent and Trademark Office*